United States Patent

Sodickson et al.

[11] 4,059,405
[45] Nov. 22, 1977

[54] METHOD AND APPARATUS FOR ANALYSIS OF CONSTITUENT CARRIED IN FIBROUS MEDIUM

[75] Inventors: Lester A. Sodickson, Newton, Mass.; Franklin Lim, Richmond, Va.

[73] Assignee: Damon Corporation, Needham Heights, Mass.

[21] Appl. No.: 715,855

[22] Filed: Aug. 19, 1976

Related U.S. Application Data

[63] Continuation-in-part of Ser. No. 243,068, April 11, 1972, abandoned, and a continuation-in-part of Ser. No. 498,646, Aug. 19, 1974, abandoned.

[51] Int. Cl.² .................. G01N 21/24; G01N 33/16
[52] U.S. Cl. .................................. 23/230 R; 23/253 R
[58] Field of Search ............ 23/230 R, 230 B, 232 R, 23/253 R; 162/158, 168; 356/209

[56] References Cited

U.S. PATENT DOCUMENTS

| | | | |
|---|---|---|---|
| 2,812,243 | 11/1957 | Goody | 23/253 R |
| 2,866,761 | 12/1958 | Hill et al. | 252/431 R X |
| 3,036,893 | 5/1962 | Natelson | 23/230 R |
| 3,216,804 | 11/1965 | Natelson | 23/253 R |
| 3,245,306 | 4/1966 | Potter et al. | 356/209 |
| 3,502,438 | 3/1970 | Natelson | 23/253 R |
| 3,526,480 | 9/1970 | Pindl et al. | 23/253 R |
| 3,691,017 | 9/1972 | Brown et al. | 23/253 R X |
| 3,721,501 | 3/1973 | Atkinson et al. | 23/230 R X |

Primary Examiner—Robert M. Reese
Attorney, Agent, or Firm—Kenway & Jenney

[57] ABSTRACT

An optically-thin preparation of a sample solution and chemical reagents produces a constituent-manifesting reaction product that can be measured in linear relation to the concentration of the constituent of interest. A fibrous sheet contains the sample and the reagents for both the reaction and the measurement. The same site on the fibrous sheet which bears the reacting materials serves as a blank to produce a reference signal for the measurement.

36 Claims, 16 Drawing Figures

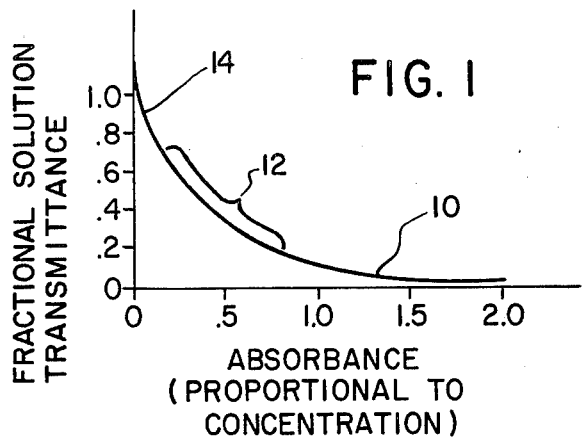
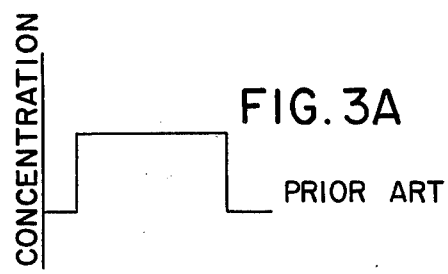
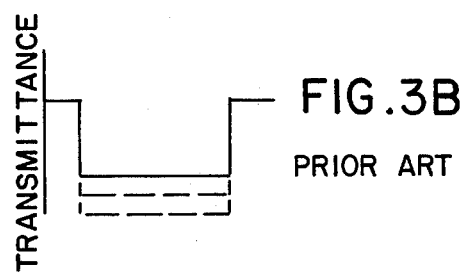
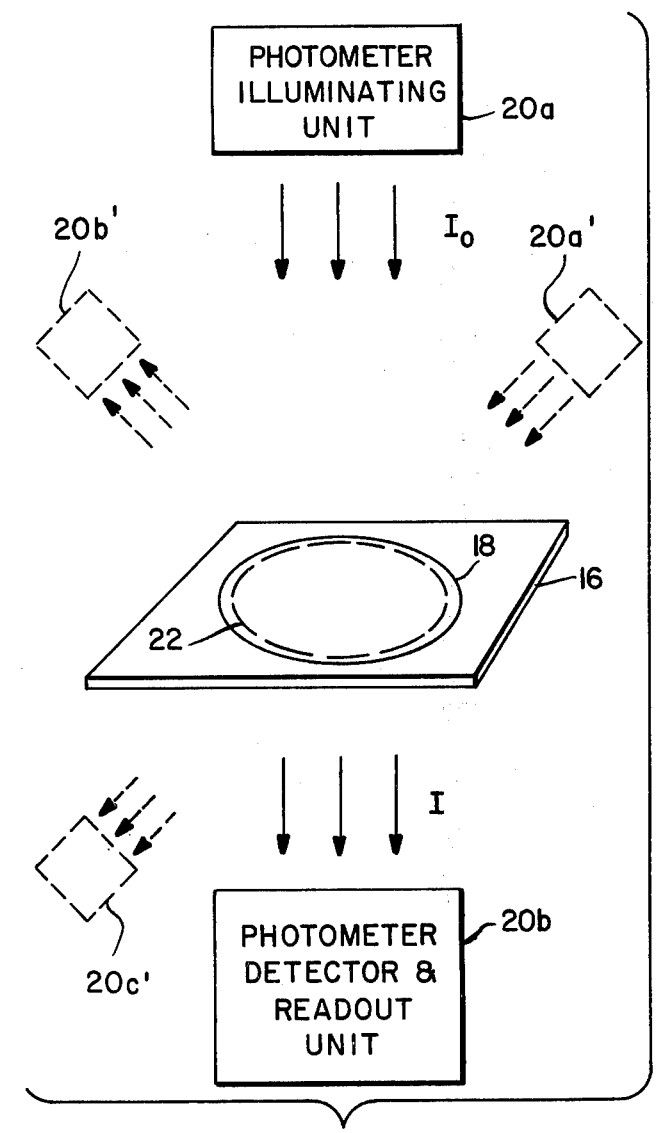
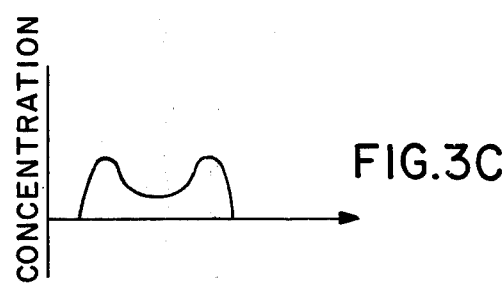
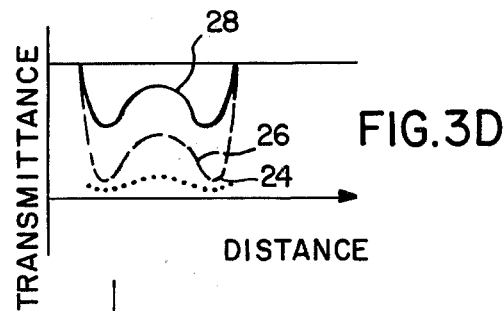

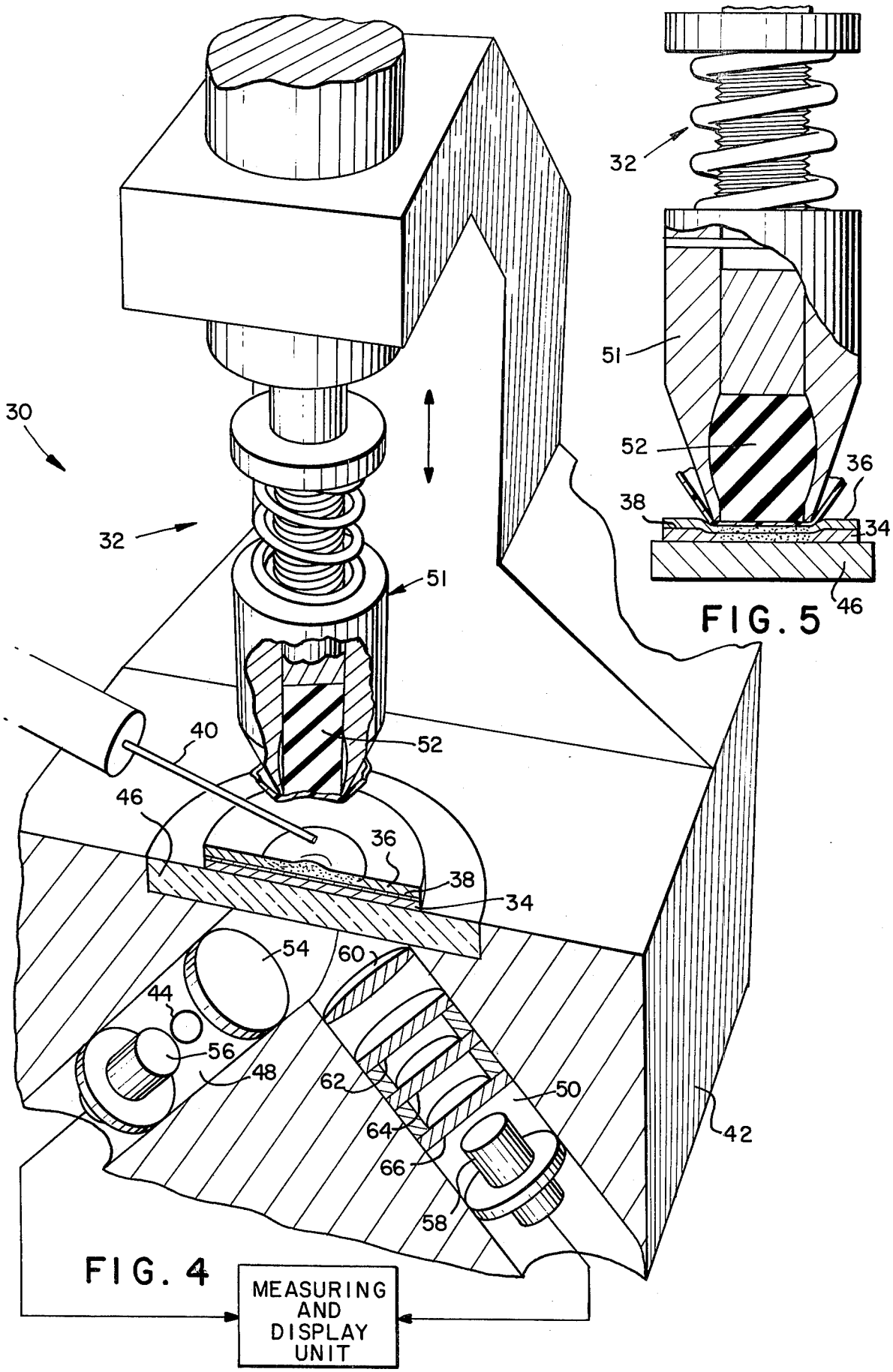

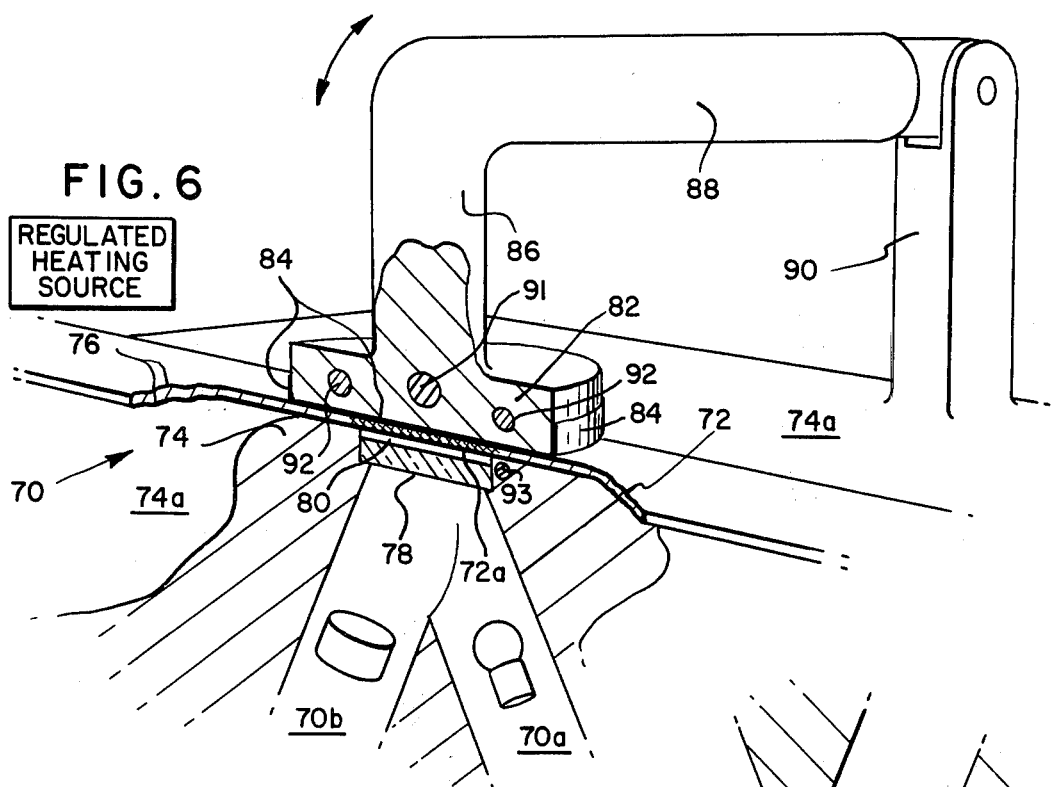

METHOD AND APPARATUS FOR ANALYSIS OF CONSTITUENT CARRIED IN FIBROUS MEDIUM

BACKGROUND

This application is a continuation-in-part of the copending application Ser. No. 243,068 for "Method For Constituent Analysis With Thin Layer Reactant Mixture," filed Apr. 11, 1972; and now abandoned; and of the copending application Ser. No. 498,646 for "Method And Apparatus For Constituent Carried In Fibrous Medium" filed Aug. 19, 1974, and now abandoned.

This invention relates to a method and apparatus for measuring a soluble constituent of a material such as a biological fluid. More particularly, the invention provides a constituent-measuring method in which the sample material being analyzed is subjected to a constituent-manifesting chemical reaction in an optically-thin layer or other distribution of the reactants, and the reactants are carried in a fibrous medium such as paper. The reactants are examined under electromagnetic radiation with sensing means that responds in a known and preferably linear manner to the concentration of a selected constituent-manifesting product of the reaction. The invention also provides an instrument for practicing the aforesaid method.

The invention enables the foregoing measurements to be made repeatedly with precision even when the apparent background absorbance or emittance of the fibrous medium which supports the reaction mixture is relatively high and varies signficantly from one test site to another, and when the spatial distributions of the material being analyzed and of the reaction-producing reagents are not all uniform and vary from one another, so that the reaction product is not uniformly distributed. The technique yields repeatable measurements provided that the relative distributions are the same for successive samples. Moreover, the procedures of the invention provide highly sensitive measurements of constituent concentrations as contrasted to the prior art.

Prior art regarding the invention includes the teachings in the U.S. Pat. Nos.: Yagoda, 2,129,754; Natelson, 3,331,665; Natelson, 3,036,893; Natelson, 3,368,872; Natelson, 3,216,804; Natelson, 3,502,438 ; Natelson, 3,219,416; Ray, 3,526,479; Natelson, 3,260,413; Findl, 3,526,480; Natelson, 3,261,668; Fetter, 3,552,925.

An object of the invention is to provide an improved method and apparatus for measuring constituents of a biological fluid contained in a fibrous medium. A more particular object of this invention is to provide a method and apparatus for monitoring a chemical reaction, and/or measuring a reaction product, contained in a fibrous medium with minimal dependence on the uniformity of the distribution of reactants.

A further object is to provide a procedure and instrument for measuring one or more soluble constituents of a fluid material contained in a fibrous medium and which provides higher sensitivity than the prior art.

Another object is to provide a method and apparatus of the above character that can employ as the reaction and analysis vessel a fibrous sheet member that is free of material-constraining structure, such as a disc of confined size or constraining rings on the sheet member.

Another object of the invention is to provide a method and apparatus of the above character in which the fibrous analysis vessel can have one or more test sites that are unbounded.

It is also an object of the invention to provide a method and apparatus of the above character capable of precise and accurate constituent measurement.

It is a further object of the invention to attain the foregoing measurement results with unbounded test sites and with minimal loss of precision due to variations in the volumes of the reactants added to the test site.

An additional object of the invention is to provide a method and apparatus of the above character that requires only a small volume of the original sample material, often less than one microliter.

Another object of the invention is to provide a method and apparatus of the above character capable of providing analyses rapidly, and further with minimal setup.

A further object of the invention is to provide a method and apparatus of the above character that can perform both rate-reaction measurements and end-point measurements.

Other objects of the invention will in part be obvious and will in part appear hereinafter.

SUMMARY OF THE INVENTION

In brief, the invention provides an analysis procedure in which reagents and a sample solution combined on a fibrous medium chemically react to produce a reaction product that is a known measure of a constituent of the sample solution. Upon illumination of the layer with electromagnetic energy of a selected wavelength, a radiation detector or other energy-sensing means having a known and preferably linear response provides a linear or other known measure of the concentration of the constituent of interest. The reaction mixture is adjusted so that the concentration of the reaction product at its most dense point is so low that it absorbs only a small fraction of the radiation traversing the fibrous medium.

The reagents and the sample solution are spatially distributed so that, ideally, the amounts of the various reactants are balanced with each other throughout the test area for optimum chemical interaction to produce the reaction product of interest. Preferred chemical systems produce rate reactions, and it is desired to maintain optimal conditions of chemical balance across the field of view of the measuring instrument. The fibrous sheet contains the reactants for incubation and presentation to the measuring instrument. With this arrangement, the balanced distribution of reactants often involves delivering the reagents to the reaction site on the fibrous medium in a selected sequence, and not necessarily with uniform or identical distributions. This is done to overcome the chromatographic migration of reactants when subsequent solutions are added.

Also, in at least many instances of the practice of the invention, the reaction sites do not require a confining structure such as a Yagoda ring. Instead, the reaction site can be unbounded.

The invention also provides equipment for the preferred practice of the foregoing procedure. In general, the equipment provides self-adjusting and repeatable optical coupling from a radiation source to a radiation sensor by way of the reactant-bearing fibrous medium. This coupling remains uniform over the time course of the chemical reaction. To this end, the equipment supports the fibrous sheet in an essentially fixed geometry at a fixed location. Also, the equipment retards evaporation of liquid from the fibrous sheet, at least during the measuring interval, and prevents undue compression of the reactant bearing site.

In addition, the practice of the invention can employ the apparatus described in the copending, commonly-assigned patent application Ser. No. 243,028, entitled "Press For Progressive Compression Of Liquid-Bearing Absorbent Article" (U.S. Pat. No. 3,844,717 issued Oct. 29, 1974) of L. Sodickson and F. Lim filed concurrently with the above-noted prior application Ser. No. 243,068. The press structure of the Ser. No. 243,028 application can be used to deliver a protein-free ultrafiltrate of a sample solution such as blood serum or whole blood for analysis in accordance with the invention described herein. Further, the fluorometer structure of the copending application can be used to advantage in the practice of the invention.

One advantage of performing chemical constituent analyses in accordance with the invention is that it requires little time, particularly as compared with prior techniques. Further, the practice of the invention requires a minimal amount of equipment. For example, in the lactate analysis of whole blood with a fibrous medium already treated with analysis reagents as described below, the desired serum ultra-filtrate of the blood sample can be transferred to the reagent-bearing medium by means of the ultrafiltration press described in the Ser. No. 243,028 application identified above, and the entire lactate analysis from a finger puncture to analytical result can be completed in a matter of 3 to 5 minutes.

Considered in further detail, an objective of this invention is to provide a fast, simple, and low cost improved chemical spot test or analysis, i.e. the measure of the production of the product of a chemical reaction occurring in liquids contained in a fibrous medium. The measure of reaction product can be made either at the end of the reaction, i.e. an end point measurement, or during the reaction, i.e. a rate reaction measurement. Further, the invention is directed primarily but not exclusively to measurements by means of radiant energy, i.e. by photometric techniques in response to absorption or to fluorescence.

The photometric measurement of chemical reactions of materials contained in a fibrous medium, such as paper or a similar fibrous sheet, has long been pursued because of the ease in handling such a medium and because of its low cost, particularly as a disposable medium for analysis. When used in conjunction with the press of the Ser. No. 243,028 application, the present invention allows the collection of specimens on filter paper and subsequent analysis without need for centrifugation, as is commonly required in the prior art.

However, several problems have made it difficult to obtain the desired measurements with the required accuracy and repeatability. One problem is that the paper or other medium produces a high-level background photometric signal that varies significantly from one reaction site to another, and even within a site. In particular, investigators in the field of paper chromatography have reported large variations in optical transmission, optical reflectance, and native fluorescence from point to point an analytical paper sheets. This location-dependent background signal seriously degrades the precision of measurement of the reaction-responsive signal of interest in chemical spot-test analysis. Moreover, efforts to resolve this problem for paper chromatography have not been applicable to the somewhat different art of chemical spot-test analysis.

In spite of this problem, the prior art as set forth in the above-noted Natelson U.S. Pat. Nos. 3,036,893 and 3,502,438 and the Findl et al U.S. Pat. No. 3,526,480 teaches that the unknown concentration of a chemical constituent in a specimen be determined by comparing the observed optical measure developed on a reagent-bearing site of a fibrous sheet exposed to the specimen of interest with the corresponding optical measure of a similar site exposed to calibration solutions of known concentration. The achievement of repeatable and accurate quantitative results in this manner presupposes that the measured difference in the optical property at the several sites produced by the chemical reaction in proportion to the desired constituent concentration be large compared to the background optical difference already present in the fibrous sheet at these sites.

The above-noted prior art also indicates that the non-uniform distribution of reactants within a test site is a primary source of error. This art accordingly teaches a variety of techniques that are asserted to achieve precision by rendering the distributions uniform within the instrument field of view. To this end, U.S. Pat. No. 3,036,893, for example, teaches that a solution to be analyzed be distributed uniformly over a reagent-bearing fibrous strip by applying the solution to the strip through a porous screen. The '893 patent and U.S. Pat. No. 3,526,480 also teach the advantage of a uniform distribution of reagents. However, these techniques remain subject to fluctuations in the underlying medium itself.

These prior teachings describe the well-known "ringing" phenomenon as a major limitation on the accuracy of quantitative determinations performed on fibrous sheets. This occurs in the prior art because the different concentrations of reaction product present at different portions of the optical field of view do not contribute proportionately to the measurement of interest, whether it be optical transmission or reflectance, or fluorescence.

Simply stated, the present invention recognizes that the ringing phenomenon does not hamper the measurement in this way if the ring itself absorbs little of the incident or re-emitted light. Practice of the invention thus provides that all absorbing molecules constituting the ring as well as those within the ring be exposed to essentially the same incident light intensity and do not attenuate the light emitted by neighboring molecules. However, reducing the concentration in the ring to this low a value results in a chemically produced change in the optical measure which is small compared to background differences from site to site. The prior art techniques were not satisfactory at these low absorption levels.

The present invention circumvents both difficulties by measuring the chemically produced change in optical property at each site relative to the background at that same site prior to the change-producing reaction. The resultant relative measure of test sites is then compared with that of the calibration sites. Thus, the present invention uses each reaction site as its own blank for reference purposes. The resultant measurement is essentially independent of the initial optical conditions of the fibrous medium site, and hence is responsive to a maximal degree only to the phenomenon of interest. The freedom from the adverse effects of ringing which result from this technique allows one to measure the concentration of a reaction product resulting from the direct deposition of a sample solution onto a reagent-bearing fibrous medium, in direct contrast to the prior teachings noted above. In particular, it has been found that an accurate measure can be made of the product of a reaction taking place with reactants distributed non-uniformly within a fibrous medium when the optical absorbance of the product is low, specifically well below the 0.2 minimal level usually considered necessary for meaningful measurements in classical in-vitro absorption spectrophotometry. See for example, page 344 of *Spectro-Chemical Methods of Analysis*, edited by J. D. Winefordner (Wiley-Interscience). Moreover, the measure is essentially linear in terms of the concentration of the reaction product.

The foregoing condition of low optical absorbance is referred to herein as an optically-thin condition. With reactants present in a manner that produces the reaction product of interest in this low concentration level, the sensitivity of the measurement to non-uniform distribution over the optical field of view, and particularly to ringing, is rendered negligible.

In addition to the foregoing problems, it has been found that the measurement of the optical response produced by a reaction product in a fibrous medium varies significantly with the degree of wetness of the medium and the degree of compression of the reaction site. The problem with wetness is considered to be unqiue to the present procedure, in which rate reactions are monitored in progress and hence require liquid for molecular mobility. This problem is avoided in the U.S. Pat. No. 3,036,893 patent, for example, by drying the reaction site after reaction and prior to optical measurement.

In brief then the invention provides apparatus and procedures for measuring the concentration of a selected constituent of a fluid by means of a controlled chemical reaction that produces a small modification to the optical properties of the highly variable fibrous medium background. The measurement of interest does not require uniform distribution of the reaction product over the instrument field of view, but only a distribution that is repeatable for different measurements. According to the invention, the instrument and the procedure employ a stored or "remembered" measure of the large, or apparently optically-thick, background of the fibrous medium at the reaction site as a reference for subsequent measurements made on the same site after initiation of the optically-thin change of interest. The preferred practice of the invention further provides for control of wetness and of fiber compression at the reaction site. These techniques enable meaningful measurements to be made even though the apparent absorbance of the background medium ranges from 1.0 when fully wet to 1.7 when dry.

The invention also provides preferred techniques for attaining repeatable constituent distributions within the reagent pad or other fibrous medium, and for attaining a combination or balance of constituents which yields a continuous high rate of reaction at least for the desired measuring interval. This continuous high rate of reaction results in a corresponding high sensitivity of the measurement. Further, the preferred techniques described hereinafter for practicing the invention provide a reaction which proceeds at a relatively uniform rate for a relatively long time, which enhances measuring rate reactions with high sensitivity.

The repeatable distribution is attained by the deposition of successive liquid reagents onto a fibrous medium in a selected sequence to control and compensate for the washing out of one reagent by successively applied reagents. Alternatively the concentrations of various reagents in a single solution are adjusted to compensate for differences in their spreading or affinity to the medium fibers when the solution is deposited on the reaction site and the remaining procedure performed. Further, the amounts of the several reagents are selected to yield a relatively optimum balance of all reacting constituents throughout the test site. It has been found that the relative volumes needed for this balanced condition are often different from those normally used for attaining optimum reaction conditions in liquid mixtures, i.e. in liquids contained in a vessel such as a test tube rather than in a fibrous medium subject to chromatographic separation, as is the practice of this invention.

With one preferred practice of the invention with unbounded test sites whose area exceeds the field of view of the measuring system, the capillary properties of the pre-treated fibrous medium provide a buffer zone which can draw off an excess of reagent or sample solution added to the reaction site. Under selected conditions, the resultant measurement is primarily proportional to the concentration of the unknown in the solution, and relatively insensitive to the exact volume of sample or reagent solutions added.

The invention accordingly comprises the several steps and the relation of one or more of such steps with respect to each of the others, and the apparatus embodying features of construction, combinations of elements, and arangements of parts which are adapted to effect such steps, all as exemplified in the following detailed disclosure, and the scope of the invention is indicated in the claims.

BRIEF DESCRIPTION OF DRAWINGS

For a fuller understanding of the nature and objects of the invention, reference should be made to the following detailed description and the accompanying drawings, in which:

FIG. 1 is a plot of the conventional characteristic of optical transmission through a liquid as a function of optical absorbance;

FIG. 2 is a simplified showing of the practice of the invention;

FIG. 3 shows several plots of material concentration and of the corresponding optical transmittance, both as a function of spatial distribution;

FIG. 4 is a perspective view, partly broken away, of an instrument for practicing the invention;

FIG. 5 is a fragmentary view of the instrument of FIG. 4 moved to the compression position;

FIG. 6 is a fragmentary perspective view, partly broken away, of a further instrument in accordance with the invention;

FIG. 7 is a cross-sectional view showing another construction for the analysis instrument;

FIGS. 8 and 8A are schematic diagrams of measuring circuits according to the invention.

DESCRIPTION OF ILLUSTRATIVE AND PREFERRED EMBODIMENTS

Figure 8A:
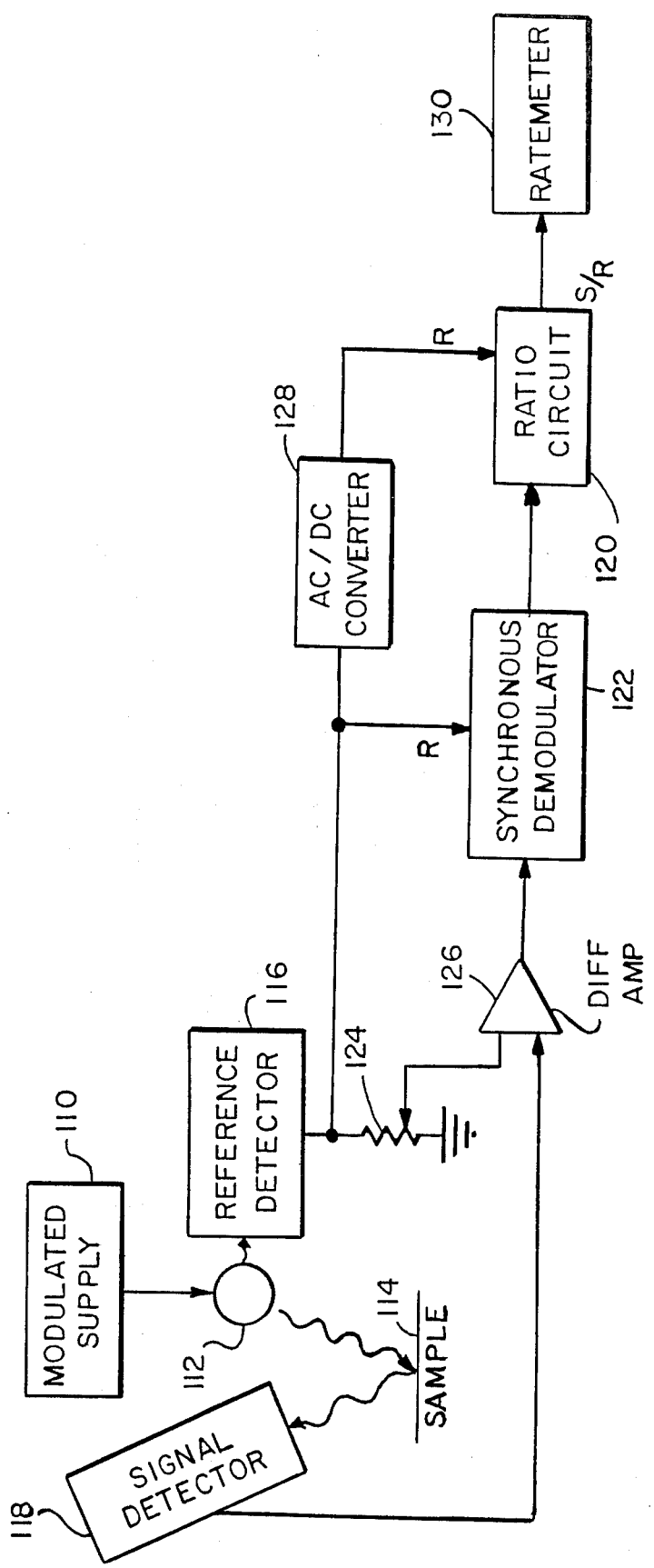

The range of optical absorbance between approximately 0.2 and 0.8 which the prior art employs for chemical spot-test analysis is shown in FIG. 1 as being along section 12 of the curve 10. The curve is a graphical representation of Beer's law in that it plots percent optical transmittance through a liquid as a function of the concentration of absorbing material in it. The optical absorbance of the liquid is proportional to this concentration, and in particular is the product of the total number of molecules along the optical path of measurement and the molar absorption coefficient of the molecules. Hence, FIG. 1 also represents the relation between percent optical transmittance and concentration of a liquid. The transmittance varies less linearly with absorbance, and with concentration, in the curve section 12 than at the upper end of the curve, i.e. than where the absorbance is less than 0.2.

Contrary to the foregoing prior practice, the present invention reveals the value of operating with a change in optical absorbance due to the reaction of interest below that of the curve section 12, and specifically in the "low-absorbance end" section 14. This section corresponds with differential absorbance values of 0.2 and less, and preferably below 0.15. This range of absorbance, and the corresponding high percent transmittance of the reactant mixture on the fibrous matrix, define an optically-thin preparation or distribution of material constituents. The condition of greater optical density which the curve 10 depicts in the section 12 and to the right thereof is termed herein as being "optically thick."

FIG. 2 depicts the practice of the invention with an absorbance photometer 20. A sheet 16 of material of continuous fibrous structure, e.g. paper, contains a liquid solution 18 of chemical reactants. The reactants are selected to produce a reaction product as a measure of a selected ingredient of the initial reactants. An illuminating unit 20a of the absorbance photometer 20 directs incident illumination, Io, on the solution in the sheet 16. An optical detector and readout unit 20b of the photometer, in optical alignment with the unit 20a and with the sheet 16, receives the resultant illumination, I, which passes through the solution-bearing sheet. The field of view 22 of the unit 20b at the sheet 16 is confined within the distribution or spread of the solution 18 on the sheet, as shown. The wavelength of the incident illumination, Io, and the wavelength of the resultant illumination, I, to which the unit 20b responds are selected to provide in the unit 20b a measure which is primarily, if not exclusively, responsive to the concentration of a selected reaction product of the solution 18.

As indicated with dashed lines in FIG. 2, the photometer can be arranged to respond to the illumination which reflects from the solution 18. That is, the illuminating unit 20a' and the readout unit 20b' can be arranged in optical alignment, typically at equal angles of incidence and of reflection, respectively, although other angles can be used depending on the diffusion of the illumination.

As FIG. 2 further illustrates, the photometer 20 can provide reflection and transmission measurements simultaneously and with a single source with an arrangement employing the illuminating unit 20a', the reflection-sensing unit 20b' and a transmission-sensing unit 20c' also in optical alignment with the source unit 20a'. Similarly, the latter arrangement can provide simultaneous measurements of fluorescence, with unit 20b', and of absorbance, with unit 20c'.

The foregoing practice of the invention which FIG. 2 illustrates is generally conventional. However, before describing the invention further, the "optical thickness" of a solution carried in a fibrous medium as this term is used herein will be described with further reference to FIG. 2.

The fibrous sheet 16 itself transmits only a small fraction of the incident illumination, which illustratively has a wavelength of 340 mm. The transmission is low primarily because of scattering by the fibers of the paper sheet, rather than due to absorption by them. In view of this phenomenon, the phrase "attenuance" has been coined to describe the effect of the sheet on the light passing through it, as distinguished from the usual "absorbance." The term attenuance thus refers to the sum of absorption by a material plus the removal of intensity from an optical beam due to scattering.

The attenuance, as well as the reflectance and the fluorescent emission, of the sheet 16 to the incident illumination has been found to have a strong dependence on the wetness and on the compression of the sheet. This can be understood when one considers the effects of liquid and of pressure on the fibers and on the interstitial spaces. Paper scatters and reflects light the most when it is dry because the interstices are occupied by air, which has a refractive index that differs significantly from that of the paper fibers. Water, however, is closer in refractive index to that of the fibers, so that as water is deposited on the sheet there is less scattering, lower reflectance, higher apparent transmittance (i.e. reduced "attenuance"), and reduced emitted fluorescence. This phenomenon is the basis for the use of translucency agents in paper chromatography, whereby fluids which match the refractive index of the paper fibers are added to a dried chromatogram to render it as transparent as possible for densitometry.

This theoretical model predicts that a beam of light incident on the sheet 16 scatters within the sheet many times before it is ultimately absorbed or emerges as reflected or transmitted light. One therefore expects that the effective path length of the light through the fibrous sheet is greater than the thickness of the sheet itself.

This extended effective path length has been observed in the course of analysis concerning the present invention. In particular, this greater path length has been observed with the apparatus described below with reference to FIG. 7 by comparing the observed fluorescence and transmission of paper discs wetted with known volumes of NADH solutions having different concentrations, with the corresponding fluorescence and transmission of the same volumes of solutions in vitro, i.e. substituted for the paper disc. The apparent increase in effective path length has in this manner been found to be between 3 and 5.

It can thus be understood that an absorbing solution placed on a fibrous medium such as paper can increase the apparent "attenuance" of light by absorbing anywhere along the increased path length. If this absorption is followed by a fluorescent re-emission, the fluorescent light must migrate through the scattering fibers in the same way as the exciting radiation, until it emerges from the sheet or is internally absorbed. Further, it is known, e.g. from U.S. Pat. No. 2,554,321 of Bray, that fluorescence measurements become non-linear if the concentration of the fluorescing substance becomes so high that the incident light beam is strongly attenuated in traversing the solution of interest. The reason for the non-linearity is that the fluorescence-producing absorption by the outer fluid, which the illumination encounters first, reduces the contribution of inner fluid to re-emitted light by decreasing the effective excitation intensity in the inner fluid.

The reference to the "optical thickness" of the solution in the present invention is based on the increased effective path length described above.

In accordance with the invention, the optical absorbance of the reaction product present in the solution 18 in the sheet 16, at the spectral range of interest, is maintained less than 0.2 and generally less than 0.15 for the effective path length defined by the scattering within the sheet at the operating wetness. That is, the effect of the solution on the sheet 16 is optically thin at the spectral region of interest, at least within the field of view 22 of the photometer unit 20b.

More particularly, FIG. 3 shows the operation of the FIG. 2 instrument with different distributions of the measured materials, i.e. the material constituents to which the photometer responds. The prior art practice, noted above, prescribes that these materials be distributed uniformly throughout the photometer field of view. The graph of the spatial distribution of the measured materials in FIG. 3A depicts such a uniform distribution. The graph of FIG. 3B shows the corresponding transmittance, i.e. the ratio of resultant illumination I to the initial illumination Io, of this distribution of the measured materials. The profile of the latter graph is identical to that of the FIG. 3A graph, as expected.

FIG. 3C shows a nonuniform spatial distribution of measured materials on the sheet 16 such as ideally results when the materials are deposited on the sheet at the center of the field of view and spread radially. The distribution has greater concentration at the periphery of the resultant "spot" than at the center, as is typically encountered with "ringing," i.e. the washing out of liquid materials from the center of a spot towards the periphery of the spot.

When the concentration of materials distributed per FIG. 3C is significantly optically thick, i.e. the optical absorbance is far in excess of 0.2 (FIG. 1), the optical transmittance of the distribution has a profile such as the curve 24 of FIG. 3D. This profile is not a linear response to the distribution profile of FIG. 3C. Rather, it is highly non-uniform, with less than proportionate transmittance from high-concentration portions of the FIG. 3C profile and with greater than proportionate transmittance from the central, low-concentration portion of the FIG. 3C profile. It is because of these non-linearities that the above-noted prior art prescribes uniform spatial distributions of the measured materials, per FIG. 3A.

With a lesser concentration of the measured materials distributed per FIG. 3C, but still in excess of an optically-thin absorbance, the resultant optical transmittance has a profile, as shown with the FIG. 3C curve 26. This profile is still non-linear relative to the FIG. 3C concentration profile, but less so than the grossly optically-thick condition of curve 24. By way of illustrative example, where the peak-to-valley ratio of the concentration curve in FIG. 3C is two-to-one, the curve 28 for the optically thin condition should have the same peak-to-valley ratio, but the curve 26 will have a lesser ratio, and the ratio for the curve 24 will be even smaller, e.g. close to unity.

Hence, the FIG. 2 instrument does not provide a linear measure of the reaction product concentration when the materials to which the measure responds are dstributed non-uniformly in an optically-thick condition. Yet the importance of being able to measure the concentration linearly becomes apparent from examination of FIG. 3E, which shows a concentration distribution which is typical of that actually encountered in spot-test analysis in the absence of the special procedure which the prior art teaches, i.e. in the practice of the present invention.

However, an essentially linear measure does result when the non-uniform distribution is optically thin. That is, when the FIG. 3C profile of spatial distribution of reaction product is optically thin, i.e. has an optical absorbance less than 0.2 at its most dense points, the corresponding profile of transmittance is a nearly linear response. The FIG. 3D curve 28 depicts this condition.

Thus the instrument of FIG. 2 can provide a substantially linear measure of concentration when the materials which absorb the wavelength of interest are present in an optically-thin layer or other condition. This finding remains valid even in the presence of other strongly attenuating backgrounds, e.g. due to the paper sheet 16 itself or in the initial reactant solution, provided that the background attenuance is constant during the interval of blank and signal measurements or varies in a known and repeatable manner from sample to sample.

Moreover, consistently precise measurements are realized from different samples of the solution 18, on different sites of the sheet 16, when the spatial distributions for the several samples are the same, i.e. are repeatable. The prior art, by contrast, considered that repeatable measures could be obtained only with uniform material distributions.

FIGS. 4 and 5 show a fluorometer 30 with which the invention can be practiced, rather than with an absorbance instrument as previously described. The considerations regarding an optically-thin condition and regarding repeatability as previously set forth with reference to FIGS. 1 and 3 apply to a fluorescence-responsive instrument. Moreover, a fluorometric measurement yields greater sensitivity than an absorbance measurement.

The illustrated fluorometer 30 of FIG. 4 is combined with a press 32 that transfers only the small-molecule fraction of a sample liquid to a fibrous sheet, where that fraction undergoes the chemical reaction desired for the measurement. The compression of the fibrous sheet by the press usually is released during the measurement. In particular, a dry, fibrous reagent sheet 34 previously treated to bear the desired reactants is layered under a further dry, fibrous, sample sheet 36 with an ultrafiltration membrane or other filter 38 between them. The liquid to be analyzed is deposited on the sample sheet, typically with a pipette 40.

As described in full in the above-noted application Ser. No. 243,028, when the press head 51 is moved in the direction of the arrow from the position shown in FIG. 4 to the position in FIG. 5, it forces a significant portion of the small-molecule fraction of interest of the sample from the sheet 36 through the filter 38 to the reagent sheet 34. The liquid fraction commences the desired chemical reaction with the reagents in the sheet 34. The fluorometer measures the reaction product of interest, on either a continuous basis as appropriate for a measurement of a rate reaction or after a selected time, whichever is appropriate.

With further reference to FIGS. 4 and 5, the base 42 of the press forms a housing for the fluorometer 30. The fluorometer illuminates the reagent sheet 34 with radiation from a lamp 44 through the platen 46 of the press; the platen is an optical window transparent to the incident exciting radiation of the lamp 44 and to the fluorescence which this radiation produces in the reaction product of interest in the reagent sheet 34.

More particularly, the base 42 has a primary passage 48 and a secondary passage 50 therein; the passages are coplanar and are angled relative to each other with their central axes converging at the sheet 34. The lamp 44 is mounted in the primary passage 48 in optical alignment through the optical window of the platen 46 with the section of the reagent sheet which is centered under the press, i.e. which is under an inner foot member 52 of the press. A primary filter 54 is mounted in the primary passage interposed between the lamp 44 and the platen 46 to block unwanted radiation from illuminating the reaction pad. Further, a reference detector 56, typically for producing an electrical signal repsonsive to the intensity and the modulation of the illumination from the lamp 44, is mounted in the primary passage, preferably out of the optical path between the lamp and the platen, as illustrated.

Although not required, the illustrated fluorometer secondary passage 50 is oriented along the angle at which incident radiation from lamp 44 reflects from the reagent sheet 34. Thus, the illustrated fluorometer 30 has the secondary passage 50 aligned at the angle at which incident energy from lamp 44 reflects from the sheet 34 surface which is contiguous with the optically-transparent platen 46. This geometry is preferred to provide essentially equal-length optical paths, from lamp 44 to the detector 58 in the secondary passage 50, for illumination impinging on all points of the reagent sheet 34 which are within the fluorometer field of view. The equal-length optical paths, in turn, result in high measuring accuracy and precision.

The secondary passage 50 mounts a fluorescence detector 58 and, in optical alignment between the detector 58 and the reagent sheet 34, mounts a lens 60 which focuses the desired fluoroescence onto the detector 58. Also mounted in the secondary passage are secondary filters 62, 64 and 66. These filters together block reflected primary radiation from the lamp 44 and block background fluorescence and other radiation above and below the pass band of the fluorescence to be measured.

Further, the secondary filters are selected to be non-fluorescing, at least in the wavelength range of measurement, when excited with reflected illumination from the lamp 44 and with whatever fluorescence is present. Dielectric and metal film filter constructions are preferrd to provide the filters 62, 64 and 66 with the desired degree of non-fluorescence. This provision of non-fluorescing secondary filters in accordance with the invention results in an increase in sensitivity and in background rejection of the fluorometer 30, as contrasted to a fluorometer of similar construction except having glass or other secondary filters which are known to produce broad band fluorescene encompassing the wavelength range of measurement.

Alternative to combining the press and photometer in a single instrument as FIG. 4 illustrates, they can be constructed separate from each other, and used independent of one another. For example, a sample liquid ready for analysis can be deposited directly on a fibrous paper sheet and reacted with reagents, to produce a reaction product which a fluorometer constructed as in FIG. 4 measures.

FIG. 6 shows the details of a preferred construction of a fluorometric instrument 70 for the practice of the invention. Although described with reference to a fluorometric instrument, the construction can be used with other forms of a photometer. The optical elements of the instrument, i.e. the lamp, filters, signal detector, and reference detector, can be arranged in optical passages 70a and 70b as described above with reference to FIG. 4; the lamp and the signal detector are only indicated schematically in FIG. 6.

However, the support for the fibrous medium and the exposure or optical coupling of the medium to the lamp and the signal detector embody further features of the invention. More particularly, the instrument 70 supports a fibrous medium illustrated as a paper strip 72 on a flat support surface 74a. A reaction site 72a of the strip, which contains the reactant mixture for producing the selected reaction product, is located between an optical window 78, which is closely recessed by a spacing 80 below the support surface, and a backing plate 82 that extends laterally beyond the site to rest on the paper strip above the support surface. An optically-transparent film 76 is wrapped around the strip 72. The film is contiguous with the upper and lower surfaces of the strip and encloses the reactant-bearing site 72a to prevent evaporation of liquid from this site. The film 76 also precludes contamination of elements of the instrument by the reactants of this strip. It hence avoids the necessity of cleaning the optical window 78, the support surface 74a and the backing plate 82 between measurements at different reaction sites. The film 76 can be of an optically-transparent, thermoplastic resin such as is produced by the polymerization of vinylidine chloride and is sold commercially under the trade name Saran Wrap.

The housing 74 that forms the support surface 74a is opaque to the radiation with which the instrument operates, and the window 78 is transparent to the wavelengths of interest. The window 78 is mounted in an aperture through the housing 74 and in optical alignment with the two optical passages 70a and 70b, which illustratively are angled at 45° relative to one another.

The backing plate 82 rests upon the paper strip 72 above the housing 84 and centered at the window 78. The illustrated backing plate 82 is hingedly mounted to the instrument housing to facilitate lifting it clear of the support plate, i.e. so that the backing plate is readily removed from, and alternatively placed upon, the paper strip when access is desired to the paper strip or to the support surface and the window. The illustrated structure of the backing plate 82 is that of a disc having a flat bottom surface. A stem 86 protrudes upward from the back, upper side of the disc to a horizontal arm 88 that is hinged to an upstanding post 90 on the housing. The backing plate serves, by its slight weight, to hold the strip 72 flat against the support surface 74a with the Saran or like film pressed to the strip. This fixes the spacing of the reaction site relative to the instrument source and signal detector. Further, the plate, together with the wrap film 76, prevents deformation of the strip at the reaction site due to the liquid thereat. Although the strip can deform slightly into the spacing 80, such deformation is small due to the restraining effect of the wrap film 76 and to the small depth of the spacing 80, which preferably is less than the thickness of the strip. By way of illustrative example, for a paper strip 0.017 inch thick, the spacing 80 is 0.01 inch (approximately ¼ millimeter). One purpose of the spacing 80 is to allow the fibrous material of the strip 72 to deform into it at the reaction site and thereby avoid significant compression of the fibrous material under the backing plate 82.

It should be noted that the weight of the backing plate on the strip is, however, slight.

With further reference to FIG. 6, the backing plate 82 is sufficiently large to rest on the dry paper of the strip 72 which is located outward of the liquid-bearing and hence wet site 72a. Hence, the thickness of the dry paper, which the plate 82 does not compress due to its limited weight, automatically determines the spacing of the plate lower surface from the support surface 74a. The plate 82 accordingly presses the upper surface of the wet site 72a to the flat and hence coplanar with the upper surface of the dry portion of the strip 72. As noted above, this action can deform the wet site slightly into the spacing 80, which is desirable because it allows the fibrous material at the reaction site to remain relatively uncompressed.

In the foregoing manner, it will be seen that the backing plate 82 fixes the location of the reaction site relative to the support surface 74a and hence relative to the photometer lamp and signal detector, as is desired. Moreover, the backing plate provides this locating function automatically and with highly repeatable precision with automatic compensation for fluctuating thickness of varying portions of the strip 72, and even from strip to strip, because it is the dry portion of the strip surrounding the reaction site which determines the spacing of the backing plate above the support surface.

A further function of the backing plate 82 is that it presents an optically-uniform surface behind the reaction site 72a. This surface can be highly reflective or highly absorbant, although a reflective surface is generally desired to produce a higher-level output fluorescent signal. The important factor is that the surface be optically uniform throughout the instrument field of view. The provision of optical uniformity also includes avoiding air gaps between the strip 72 and the backing plate, which the present structure attains.

The photometric instrument 70 of FIG. 6 further includes thermal control elements for preventing fogging within the photometer field of view due to moisture present within the reaction site 72a. In particular, fogging of the upper surface of the window 78, and of the lower surface of the backing plate 82 has been observed with an instrument as shown in FIG. 6 but lacking thermal control. This fogging is understood to develop when the lower surface of the backing plate 82 is at a different temperature from the support surface 74a or the window 78, such that liquid within the reaction site 72a vaporizes and condenses on the cooler of the window or backing plate surface. The fogging is generally undesirable because it introduces a source of error and imprecision to measurements. It has been found that the fogging can be avoided by maintaining the backing plate 82 and the window 78, together with the adjacent thermal mass of the housing 74, at the same temperature. For this purpose, the illustrated backing plate 82 has embedded therein a thermocouple 91, or other temperature sensor, and heating elements 92. The illustrated temperature sensing element 91 is centered above the window 78 and hence the reaction site 72a. These thermal elements are electrically connected to a regulated heating source. The source can be constructed according to conventional techniques to heat the backing plate to a selected, specified temperature. Where desired, however, the instrument can further include a thermistor or other temperature-sensing element 93 disposed in close thermal contact with the window 78, typically adjacent its mounting in the housing 74. The sensor 93 is also connected with the regulated source, which then energizes the heating elements 92 to maintain the backing plate at the same temperature as the window 78.

An optional element of the thermal structure of the instrument 70 is a layer 84 of thermally-insulating material on the underside of the backing plate 82. This layer is particularly desirable where it is desired that the reaction site 72a equilibrate thermally with the window 78, as when the backing plate is made of metal or other thermally-conductive material, and/or is not externally temperature controlled as by the heaters 91. The layer 84 is readily provided with the desired uniform optical property described above. In the illustrated embodiment, the layer 84 is of a plastic consisting of tetrafluoroethylene polymer such as that sold commercially under the name Teflon.

FIG. 7 illustrates a further arrangement of a photometric instrument according to the invention and for analysis of a reaction product carried in a paper disc 94. In particular, the instrument has a housing 96 fitted with an optical window 98. The window is seated within a chemically-inert elastomeric gasket 100 that protrudes above the housing surface 96a to supportingly receive a carrier sheet 102 that is apertured to seatingly support the disc 94. The aperture in the carrier sheet is sized sufficiently close to the size of the paper disc to seat the disc with a slight interference fit sufficient to carry the disc with the carrier sheet. As considered preferable, the illustrated sheet 102 is slightly thinner than the dry paper from which the disc is cut, e.g. a 0.015 inch thick carrier sheet for a 0.017 inch thick dry disc. The carrier sheet is of optically-opaque material and can be of metal shim stock.

The construction of FIG. 7 can provide an essentially vapor-tight space 106 between the disc 94 and the window 98. In particular, the window upper surface preferably is recessed below the surface 96c, as described above for the window 78 of the FIG. 6 instrument. The carrier sheet 102 is, as noted, seated on an upper rim of the gasket 100, which protrudes above the surface 96c and forms a seal therebetween.

The disc 94 can be enclosed with film such as the film 76 described above with reference to FIG. 6 to prevent evaporation from it. Alternatively it can be used without such a wrap, and evaporation from it restricted to the small sealed space 106 between the carrier sheet and the window 98.

The illustrated photometric instrument of FIG. 7 has an optical window 104 overlying the disc 94 and the carrier sheet 102. The window 104 can be seated against the carrier sheet or secured thereto, or spaced thereabove. With either construction it provides an optical passage from the reactant-bearing disc 94 to further optical apparatus (not shown) mounted within passages 108a and 108b of further housing 108. The further optical apparatus can, for example, include a fluorescence or an absorbance detector where it is desired to measure the transmittance properties of the disc 94. By way of illustrative example, the arrangement of FIG. 7 has been used with an optical source in passage 96b, a fluorescence detector in passage 96a, and an absorbance detector opposite the source in passage 108a. Alternatively, of course, the disc-supporting structure of FIG. 7 can be used with an instrument as described above with reference to FIG. 6, and the second window 104 replaced by an opaque backing plate.

As noted above, the invention resolves the point-to-point variations in the optical properties of the reactant-bearing fibrous medium by using each reaction site as its own blank fo reference purposes. That is, the same optical property which is being used to measure the reaction product of interest is measured for the fibrous medium at the reactant-bearing site prior to production of that reaction product. This measure identifies the desired optical property of the fibrous medium site at which the reaction product of interest will be produced, and with that site wet with all the reactants that are present just prior to production of the constituent being measured. Accordingly, this measure identifies the background optical parameter that is present at the reaction site when the reaction of interest is occurring. Comparison of this measure with the same measure taken subsequently, i.e. during the reaction of interest, produces a resultant signal that is responsive essentially exclusively to the reaction product of interest. Hence, the resultant comparison signal has minimal dependence on the optical background in the presence of which the product of interest is being produced.

FIG. 8 illustrates a preferred circuit for carrying out the foregoing blanking procedure. A modulated supply 110 energizes a photometer source 112 with alternating voltage to illuminate a sample 114, e.g. the constituent of interest at a fibrous reaction site, and illuminates a reference detector 116. The lamp is modulated by the supply 110 at a frequency far removed from 60 Hertz and harmonics thereof to preclude interference from power lines and like sources at that frequency. A signal detector 118 responds to resultant output illumination from the site to develop a sample-responsive signal, S, which it applies to a ratio circuit 120. The ratio circuit also receives a reference signal, R, which the detector 116 develops in response to the lamp illumination. A synchronous demodulator 122 receives the resultant ratio signal, which is proportional to the amplitude ratio S/R and is free of fluctuations or other components due to spurious variations in the source output illumination.

The demodulator, which is synchronized by the reference signal, demodulates the alternating ratio signal to remove the initial alternating modulation which supply 110 imparted to the lamp illumination. The modulator output is thus a direct current signal, which is applied to one input of a differential amplifier 126. The illustrated measuring circuit hence has the modulated supply and the demodulator 122 to avoid 60 Hertz interference, and employs a ratio circuit 120 to preclude errors due to lamp fluctuations.

The FIG. 8 circuit also has an adjustable voltage divider 124 that applies a direct voltage of magnitude $k$, equal to the value of S/R at time $t = 0$, i.e. prior to the development of the reaction product of interest, to another input of the differential amplifier 126. The response of the amplifier to these signals is the desired difference signal, proportional to (S/R − $k$), which is applied to a rate meter 130 for further processing, recording or display as desired.

The voltage divider 124 and the differential amplifier 126 provide the above-noted blanking of the high background from the sample bearing site 114. For this operation, the voltage divider 124 is adjusted, either manually or with known automatic feedback techniques, to null the amplifier 126 output signal prior to the measurement of interest. A preferred procedure is to adjust the divider for null amplifier output during the incubation period of the reaction of interest, i.e. immediately after the reactant solution is developed at the reaction site 114, but prior to production of the constituent being monitored. The voltage divider as thus adjusted serves to store information identifying the optical background of the site 114, and measured with the same optical wavelength as the reaction product of interest.

The measuring circuit of FIG. 8 is illustrative of many configurations which can, within the known skill of the art, be constructed to provide the foregoing operation. For example, FIG. 8A shows a configuration that uses a d.c. ratio circuit.

From the foregoing description it will be seen that the invention typically is practiced by introducing a liquid sample solution containing a material to be analyzed as a solute to a selected site on a fibrous sheet that serves as the analysis vessel, i.e. to contain the reaction mixture in the field of view of the measuring instrument. Multiple chemical reagents are introduced to the fibrous medium either prior or subsequent to introduction of the sample solution. The sample solution and each reagent are introduced to the fibrous medium so that each has substantially the same spatial distribution of concentration for every performance of a given test or analysis. That is, in performing an analysis on multiple samples in accordance with the invention, the spatial distribution of different samples across the several fibrous reaction sites is the same, i.e. repeatable. So also the spatial distribution of each reagent is the same for testing each sample.

The fibrous medium contains the sample solution and the reagents in an optically-thin condition. This makes it possible to measure the constituent of interest by examination of the reaction mixture with electromagnetic energy and to secure a response that is essentially linearly related to the unknown constituent concentration.

As stated above, the result of having an optically-thin distribution of sample solution and reagents in the fibrous medium is that the transmission of the incident energy, and of the detected output measuring energy, at every point in the field of view of the measuring instrument, vary essentially linearly with concentration of the constituent of interest up to the maximum concentration that is to be measured.

The constituent-manifesting reaction product of interest produced in the reaction mixture under the foregoing conditions is preferably measured with a fluorometer or other radiant-energy responsive instrument that has a linear response to the concentration of the substance of interest.

More particularly, in examples set forth below, the reaction mixture of the invention produces a fluorescent reaction product with a concentration responsive to the concentration of the unknown substance being measured. Upon illumination from the fluorometer source, at every point in the fluorometer field of view the constituent-measuring reaction product in the reaction mixture fluoresces with an intensity that is linearly proportional to concentration so long as the solution containing it is optically thin over the effective path length through the paper, i.e. fibrous medium. The fluorometer detector has a linear response to this radiant fluorescence from every point in its field of view and hence produces an electrical signal that is a linear function of the product of the fluorescent energy and the fluorometer sensitivity profile integrated over the area of the fibrous surface within the fluorometer field of view. The fluorometer sensitivity profile is the spatial distribution of the instrument's response over its field of view to fluorescence from its lamp. Hence the profile is a composite of the spatial characteristics of the fluorometer lamp and of the fluorometer detector.

As noted above, the fluorometer of FIG. 4, as well as the instruments of FIGS. 6 and 7, has equal spectral angles for the incident energy and for the measured fluorescent energy. This is desired to provide the instrument with a composite, i.e. lamp and detector, sensitivity profile which is symmetrical and approximately uniform about the detector boresight axis, albeit with some variation radically from this axis, to measure all points in the fluorometer field of view uniformly. That is, with the fluorometer angle of incidence equal to the angle of sensed radiation, the total optical path from the fluoroscent source of the reaction layer and then to the fluorometer detector is essentially uniform, at least to a first order, for all points within the fluorometer field of view.

Alternative to either an absorbance photometer or a fluorometer, the invention can be practiced with an oscillometer that measures the interaction of reaction mixture components with an oscillating electromagnetic field. For example, the fibrous sheet can be placed between two flat electrodes to form in effect a flat-plate capacitor. The instrument is calibrated to measure the change in capacitance due to the reaction product of interest at a selected frequency.

The fibrous material that contains the reaction mixture for practice of the invention is preferably of fibers that are inert to the sample solution and to the analysis reagents, and which are non-absorbing and are transparent to the electromagnetic wavelengths involved in the measurement. However, these requirements are not mandatory, rather they facilitate factors such as calibration and measuring precision, and enhance measuring sensitivity. By way of example, the invention has been successfully practiced with fibers of cellulosic material as well as of fiberglass.

Fibers of glass, i.e. fiberglass, tend however to be sufficiently fragile so that they break upon being compressed with the press described in the Ser. No. 243,028 application noted above. Accordingly, where such a press or other structure that subjects the fibrous material to stress is to be employed, it is considered preferable that fragile fibers not be used or at least that the fibrous sheet have a mixture with less fragile, e.g. cellulosic, fibers.

For measurement of a rate reaction, the sheet of fibers preferably has a fiber structure such that all liquid reagents involved cease spreading within the sheet in a time that is short compared to the time during which the reaction of interest proceeds linearly. This is because the linear portion of the reaction should proceed in large part after all the reactants have ceased spreading due to capillary action of the fibers. In the measurement of a typical rate reaction, it is desirable that approximately three-quarters of the linear portion of the reaction time take place after significant spreading ceases.

Although described with specific reference to practice with porous sheets of fibrous structure, the invention can be practiced with other porous materials. In particular, chemical spot test analysis can be performed according to the invention on a porous medium such as is used for electrophoresis, chromatography, or filtration, and which (1) is chemically compatible with the reagent system, (2) absorbs the fluids into its interstices, and (3) has sufficiently high optical scattering and sufficiently low optical absorption at the wavelength or wavelengths of interest so that there are multiple scattering interactions of light with the medium which cause the light to traverse the reaction product held in its interstices with an effective path length greater than the physical thickness of the medium. Illustrative examples of such other media can be used, preferably in sheet form, include cellulose polyacetate membranes as marketed by the Gelman Instrument Company under the registered trademark Sepraphore; cellulose nitrate microporous membrane filters as available from the Sartorius Corporation under the designation SM11304; cellulose acetate electrophoresis membranes as marketed by Instrumentation Laboratory, Inc.; and thin layer chromatography plates such as the registered Avicel Uniplate brand available from Analtech Inc. (microcyrstalline cellulose media), and the silicic acid type instant thin layer chromatography media available from the Gelman Instrument Co. under the designation ITLC SA.

With further regard to the spreading of fluid materials within the fibrous sheet, it is desired that all materials move through the sheet at the same rate. Otherwise, the distributions of various reactants tends to become unbalanced at different locations within the reaction and analysis site. In view of the vastly different flow characteristics of materials typically involved in constituent analyses, this objective often may not be realized to the desired extent. However, it has been found that disparate spreading of different materials can in many instances be limited by applying the materials to the fibrous medium in a selected sequence. In particular, it has been found that the application of large-molecule reagents, with or without drying, prior to the application of reagents of smaller molecules substantially diminishes the spreading of the reagent applied first by the latter-applied reagent. That is, it has been found that where a solution of small-molecule constituents is delivered to a fibrous medium followed by a solution of large molecule constituents, the heavy molecule material tends to spread and push the lighter molecule material out ahead of it with the result that the small-molecule material is concentrated in an annular ring outside of the area of maximum concentration of the large molecule material. This condition is undesired and results in significantly lesser measuring sensitivity then where the procedure is reversed, as further detailed hereinafter.

As examples of fibrous sheets suitable for the practice of the invention, Schleicher & Schuell test papers Nos. 903, 903-C, 404, 410 and 25, Whatman test papers GF/A, GF, B, and GF/C have all been used successfully. In some instances Yagoda-type spot confining rings have been found desirable. In general, it appears that these rings are more desirable on non-fiberglass papers and on thinner papers. In particular, wax confining rings have been used to advantage with the Schleicher & Schuell 903-C and 410 papers, whereas good results, including high sensitivity, have been obtained with Schleicher & Schuell 404 paper without confining rings.

The foregoing comments concerning the sequence of applying reagents applies also to the addition of the sample solution.

The term sensitivity is used in connection with this invention to describe the magnitude of rate of change in sensed energy, e.g. fluorescence intensity, for a given concentration of the constituent being measured.

EXAMPLE I

As a first example of the practice of the invention, blood serum is tested to measure the concentration of glucose. The analysis uses the known hexokinase reaction

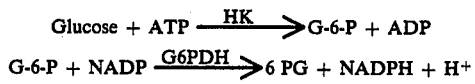

the conventional practice of which is described for example in the brochure "Diagnostic Test Combinations, Operating Instructions" distributed by Boehringer Mannheim Corporation.

EXAMPLE Ia

In the simplest procedure, a solution containing all necessary reagents is obtained by dissolving one Smith Kline Eskalab Glucose tablet in 0.5 milliliter of distilled water. Ten lambda of an appropriate dilution of the sample serum to be analyzed is deposited on a dry fibrous sheet such as S&S No. 903-C. The sample is deposited continuously, rather than drop-by-drop, at the center of the reaction site, as with a pipette. This is followed, without drying, by depositing 10 lambda of the dissolved Eskalab solution in the same continuous manner at the same spot. The order of addition is critical, as the observed initial reaction rate is three times greater in the above case than if the solution is added before the serum.

The reaction site is then monitored with a fluorometer, such as the FIG. 4 fluorometer 30, which illuminates the reaction site at 340 nanometers wavelength and observes the fluorescence with a detector responsive to the 460 nanometers wavelength of maximum NADPH emission. The fluorometer output signal is measured during the linear portion of the reaction. The measurement preferably is of the rate of NADPH production rather than of the total amount of NADPH production to facilitate the measurement of the fluorescence from the NADPH separate from the background fluorescent radiation from other materials at the test site as well as from the fibrous sheet itself. The latter radiation is essentially time invariant, whereas the fluorescence from the NADPH increases with the increase in NADPH production. Also, care is taken to avoid compressive contact of the fluorometer end window with the fibrous material and the reaction mixture to avoid variations that otherwise arise in the detected fluorescence.

Figure 9A:
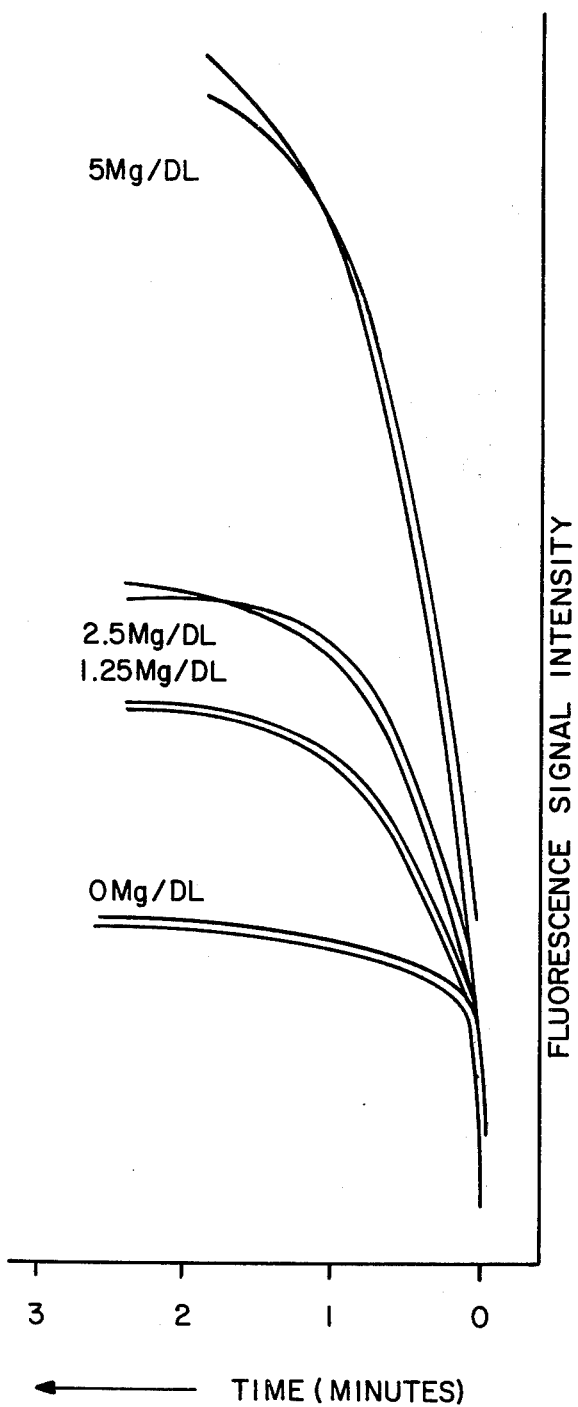
FIGS. 9 and 10 are graphs illustrating the practice of the invention.

FIG. 9a shows the variation of observed fluorescence signal above the background fluorescence of the 903-C paper as a function of time after the deposition of the reagent solution. Several different glucose standard reagent solutions were used as samples. These were prepared by dilution of a 150 Mg/Dl* stock solution, diluted 1/30 with deionized water to yield samples with concentrations of 5 Mg/Dl, 2.5 Mg/Dl, and 1.25 Mg/Dl, as noted on the Figure. The sensitivity of the resultant measurements is sufficiently high so that human sera which lie within the normal range of 65–110 Mg/Dl, would require dilution of 1/30 to fall in the operating range of this chemistry.

*It should be noted that as used herein, "Dl" means one-tenth liter, and "Mg" means milligrams.

The curves depict fluorescence that increases rapidly through an approximately linear portion which ends at about 45 seconds. The initial slopes are proportional to concentration. The observed slope for water as sample, i.e. 0 Mg/Dl, shows a significant variation in the first minute which results from a variation of the optical coupling between the backing plate, fibrous medium and fluorometer window.

A set of 17 assays was done at the four levels shown in FIG. 9a. The observed initial slopes gave a linear fit to concentration with a correlation coefficient of 0.962. Four of these measurements were made at the 5 Mg/Dl level, and gave a standard deviation of 0.5 Mg/Dl. By way of comparison, the standard deviation of the background fluorescence of the dry paper prior to administration of sample and reagents when converted to clinical units via the fitted linear regression line was 1.0 Mg/Dl or approximately double that observed for the rate reaction measurement.

EXAMPLE Ib

The reagent system of Example I was reformulated to minimize differential spreading and wash-out as discussed hereinabove to optimize it for the maximum linear period possible. It was prepared from the following basic ingredients in deionized water in the following proportions.

| Constituent | Concentration (Quantity/ml) | Commercial Designation |
|---|---|---|
| pH 7.5 Buffer | | |
| Tris(hydroxymethyl) aminomethane hydrochloride | 0.38 m (milli) moles | Sigma Trizma T4003 |
| Succinic Acid | 0.12 m moles | JT Baker #0346 |
| Magnesium Chloride | 0.16 m moles | Sigma M-0250 |
| Glucose-6-phosphate dehydrogenase (G-6-PDH) | 20 IU (International Units) | Sigma Bakers Yeast Sulfate Free Type XU # G-6378 |
| Hexokinase | 25 IU (International Units) | Sigma Bakers Yeast Sulfate free Type F-300 #H-4502 |
| Adenosine Triphosphate (ATP) | .02 m moles | Sigma #A-3127 |
| Nicotinamide-adenine dinucleotide-phosphate (NADP) | .02 m moles | PL Biochemicals #900 |

To prepare the reaction sites, 20 microliters of this reagent solution are deposited on dry unbounded type 903-C paper, and the paper then dried in a vacuum desiccator. The reagent solution and dried strips are stable for at least one month when frozen.

Figure 9B:
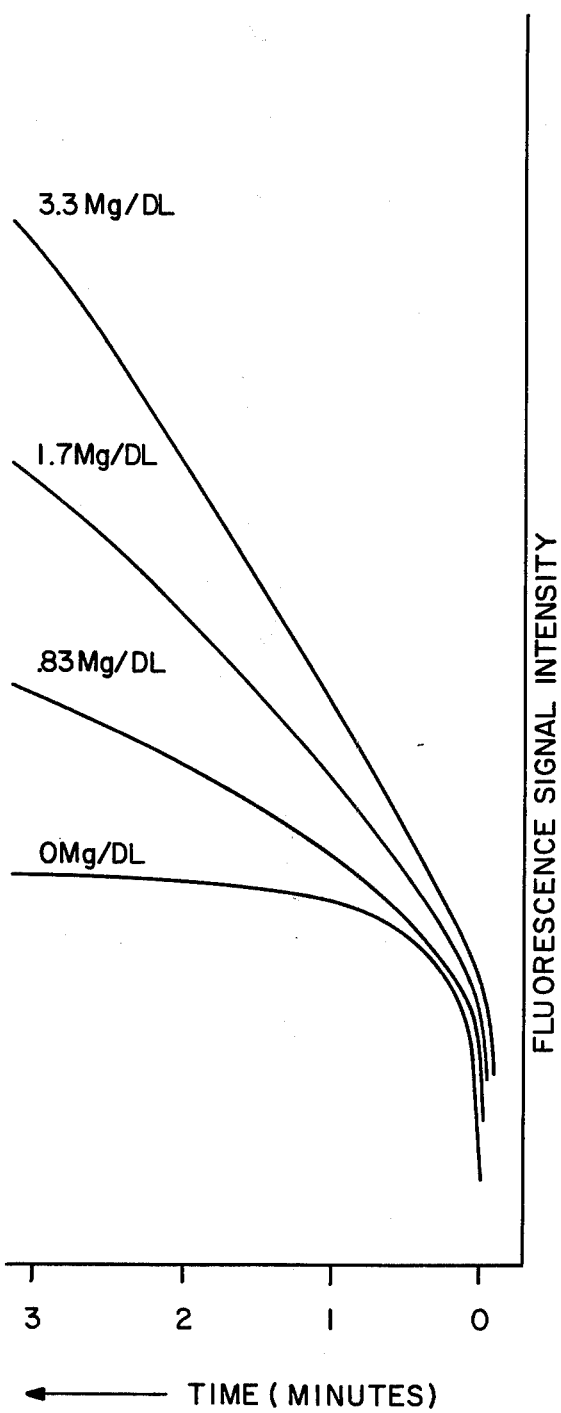

To perform a measurement, an unused reaction site at room temperature is placed over the window of the fluorometer of FIG. 6, and 20 microliters of solution are deposited as above on the center of the treated zone. A layer of saran wrap or other thin, optically transparent, plastic film may be placed on both sides of the paper to eliminate direct contact of the liquid with the fluorometer window and backing plate. This prevents carryover of specimen from one assay to the next, but does not affect the optical measurements. The film also maintains wetness at the site constant by preventing evaporation. The resulting rate reaction curves are shown in FIG. 9b for three concentrations and for water. They are most linear in the one to two minute time frame, and useable at least out to three minutes. The observed response with water as the sample shows similar behavior to Example Ia, but the measurement can now be made after the physical situation has stabilized at 1 minute.

EXAMPLE Ic

A slightly different result is obtained by pretreating the type 903-C paper with a high molecular weight polymer to minimize the absorption of solution into the paper fibers themselves. As one example, inch wide by 8-inch long strips are soaked in an aqueous solution of 6 Mg/ml of polyox resin, grade WSR-205, (molecular wt. 600,000), which is a high molecular weight, crystalline, ethylene oxide polymer obtained from the Union Carbide Corporation. That company advises that the following issued U.S. patents contain disclosure of this resin and its manufacture, U.S. Pat. Nos.: 2,866,761, Hill et al; 3,030,315, Bailey; 3,214,387, Hill et al; 2,897,178, Hill et al; 3,062,755, Hill et al; 3,274,129, Bailey; 2,991,229, Ivison; 3,085,071, Bailey.

The soaked strips are then dried in a vacuum desiccator. The dry polyox paper is slightly thicker than untreated type 903-C paper, measuring 0.019 inches in thickness rather than 0.017 inches.

The treated paper shows significantly reduced spreading of liquid placed on it, which is considered desirable. The presumed reason for this advantage is that the treated fibers do not absorb fluid and carry it outward. When 10, 15 and 20 microliters of liquid are applied to different sites, the diameters of the resulting translucent spots are 0.375, 0.450 and 0.475 inches respectively for untreated paper, but only 0.325, 0.375 and 0.400 inches for treated paper.

Thus, the polymer resin reduces capillary spreading of the fluid. Moreover, the liquid-carrying capacity of a punched disc of the treated paper appears to be approximately 10-15 percent higher than with untreated paper. A 0.375 diameter disc of untreated paper holds roughly 38-40 microliters of liquid without spilling over, while the treated paper will hold 42-45 microliters.

The reaction sites on the polyox treated 903-C paper are prepared as in Example Ib. However, since the paper holds more fluid, 30 microliters of the optimized reagent are deposited on the desired spots and subsequently vacuum dried.

The reaction is again run on the fluorometer of FIG. 6 by centering the dry spot over the optical window, again using a thin plastic film to prevent carryover and evaporation, and depositing 20 microliters of glucose solution as before.

The results are very similar to those of FIG. 9b, except with the time scale doubled, i.e. to 6 minutes. The curve for water becomes flat at two minutes, and the slope of the higher curves is approximately double that of FIG. 9b, thereby indicating roughly twice the chemical sensitivity. The observed slope with water in the first two minutes resulted from a fogging of the saran wrap (or backing plate itself if saran wrap is not used) which blocks the optical coupling to the backing plate. This was caused by a temperature differential of roughly 5° C between the backing plate and the window when the data were taken. The slope of the blank was greatly reduced when the backing plate was heated to a temperature closer to that of the window. The standard curve is linear to approximately 60 Mg/Dl (1/30 dilution) so that patient sera would have to be diluted by a factor of 50-100 to ensure that the normal range of 65-100 Mg/Dl would lie within the linear range of measurement. Note that this measurement then would consume in the order of 0.2 to 0.4 microliters of the original patient serum, and produce the result in 2 to 4 minutes.

When the volume of glucose solution added to the dry reagent spot is varied from 15 to 30 microliters, the observed rates in the linear portion of the curves are found to vary only by a factor of approximately 1.5, rather than 2 as would be expected. (It is expected that this variation in slope can be reduced even further when the water blank is reduced by the proper temperature control.) This decrease in sensitivity to the liquid volumes facilitates practice of the invention with precise results even without corresponding precision in the dispensing of the reactant solutions.

EXAMPLE Id

The polyox treated paper and the optimized reagent can be used in conjunction with a press, constructed as described above with reference to the Ser. No. 243,028 application, to assay for glucose a whole blood sample collected on type 903-C paper. To do this, the reaction site is prepared by preforming wells in the treated paper by closing the press on the paper. A ring approximately 1 mm wide and 1 cm in diameter is very highly compressed with the center only gently compressed. Eleven microliters of the optimized glucose reagent are then deposited on the center of this well and vacuum dried. This volume reagent just fills the center of the well and does not enter the highly compressed ring.

To perform the measurement, a reagent-containing well in the dry paper is centered beneath the press and covered first with an ultrafiltration membrane and then with the paper sheet containing the dried blood spot. The blood spot is then reconstituted with 20 microliters of saline or brij water solution and the press closed for a period of 20 to 40 seconds.

During this time a small volume of ultrafiltrate containing 1 to 10 percent of the glucose persent in the blood spot passes through the membrane into the well. The volume of liquid is sufficiently small that molecular mobilities are low and the reaction proceeds slowly, if at all. When the press is opened and the top sheets separated, the spot dries. The reaction site is then placed over the fluorometer window, e.g. constructed per FIG. 6, and 15 microliters of water added to reconstitute the dry spot and initiate the reaction. This volume is again chosen so that the liquid does not enter the highly compressed ring.

The internal pressure applied by the press and the time in which it remains closed are adjusted to bring the transferred concentration of glucose into the operating range of the reaction.

EXAMPLE Ie

To further investigate the optical phenomena taking place within the fibrous medium, simultaneous measurements of UV transmission and reflected fluorescence were undertaken using the above-described polyox treated paper and optimized glucose reagent. Two optical heads were used in the configuration shown in FIG. 7 with the lamp and reference detector of the upper unit (i.e. in passages 108a and 108b, respectively) used to provide and monitor the incident 340 nm light. The detector in the lower unit (i.e. in passage 96b) was placed behind a 340 nm filter while the upper detector was placed behind a non-fluorescing filter set centered on 460 nm. To facilitate the measurement, ⅜ inch diameter discs of polyox treated paper were wetted with 11 microliters of the reagent solution and vacuum dried. These were placed in a ⅜ inch diameter hole in a 0.015 inch thick stainless steel shim (i.e. the FIG. 7 carrier sheet 102) which was held against the window (i.e. element 104) of the upper instrument by the rubber gasket (i.e. element 100) of the lower instrument. The spacing was such that the wet paper disc under analysis was in contact with the upper window, extended downward through the shim stock but did not contact the lower window (element 48). The relief space (element 106) was sealed by the gasket so that the volume in which the fluid could evaporate was limited. This air gap also acted as a thermal buffer to the cooler lower window.

Figure 10:
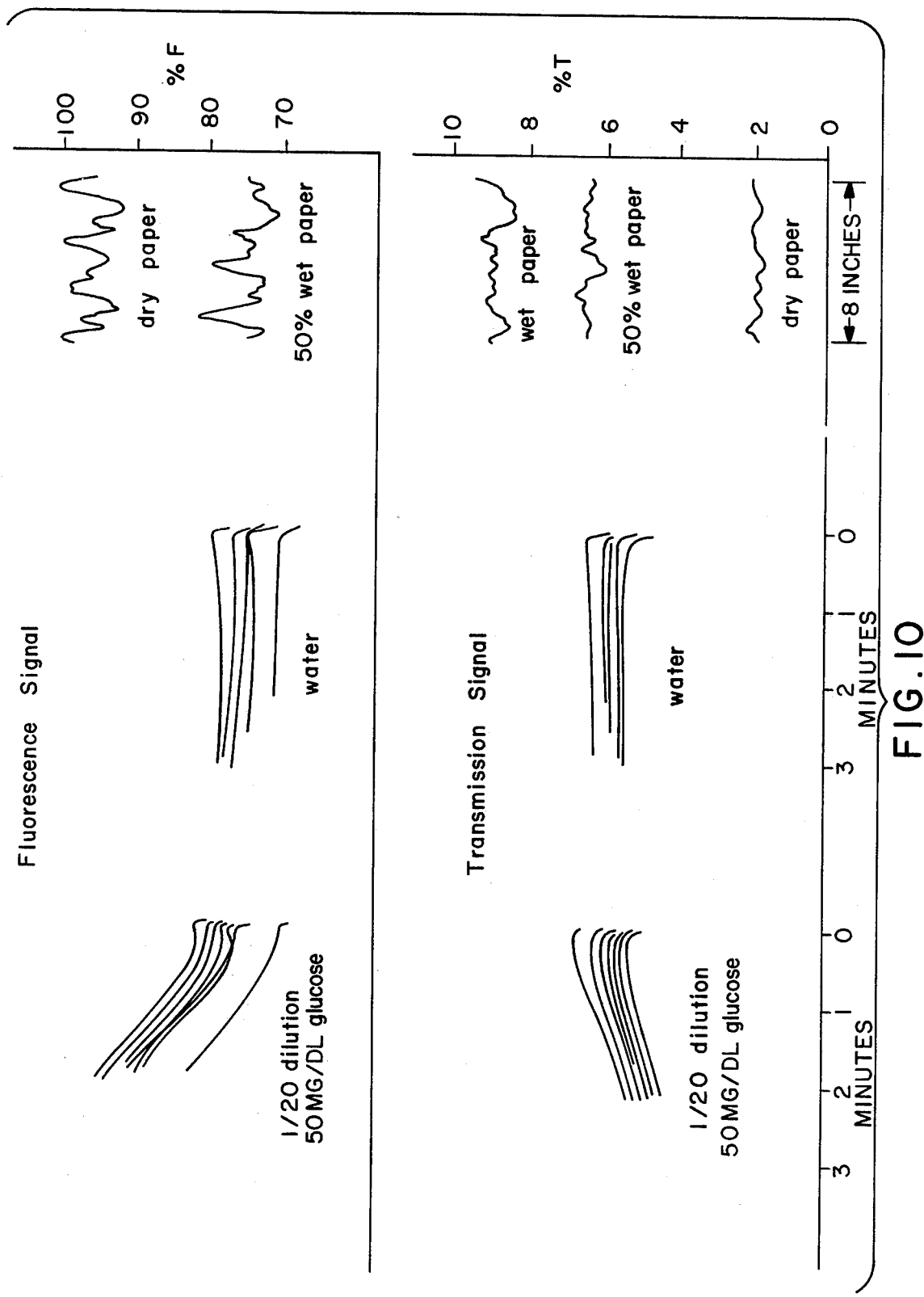

To perform the analysis, 25 microliters of dilution of a commercial serum standard (Ortho Diagnostics Instruments low AcuChem calibration fluid, lot #T) with a glucose concentration of 50 Mg/Dl were added to each of several different discs and the resulting curves recorded. Twenty-four separate assays were done at six different dilutions. Eight of these were at a 1/20 dilution and five used water as sample. The results for these two concentrations are shown in FIG. 10 along with a scan of the paper when dry, and when wet, for comparison of chemically induced changes with the native fluorescence and lower transmission of the paper.

A linear regression analysis was performed on the averaged slopes observed in each determination versus dilution. The results show that the assay is linear from water through a 1/10 dilution. The correlation coefficient is 0.998 for the fluorescence measurement and 0.995 for the absorbence measurement. The eight results at 1/20 dilution produce a standard deviation in observed rate corresponding to 2.4 Mg/Dl or 4.9 percent of the 50 Mg/Dl contained in the original fluid. The transmission measurements are almost as precise, showing a standard deviation in clinical units of 5.5 Mg/Dl or 11 percent of the 50 Mg/Dl in the original solution.

These results demonstrate that transmission measurements can be used as well as fluorescence, provided the fluctuations in attenuance of the fibrous medium from spot to spot are eliminated. These fluctuations are apparent in the differences between the starting fluorescence at $t=0$. The standard deviation of the eight initial values in the 1/20 data set is 17.9 Mg/Dl when converted to clinical units. The corresponding value for the five water assays is 16.8 Mg/Dl. Thus, the fluctuations in the starting point far exceed the change produced by the chemical reaction in one minute. These starting-point fluctuations are typical, as shown by the data in the right one-third portion of FIG. 10, which shows the observed fluorescence and transmitted signals when a 1 inch × 8 inch long strip of paper wrapped in Saran wrap is pulled through the space between the upper and lower instrument windows 98, 104 in FIG. 7, with the carrier sheet 102 removed. The 50 percent wet strip was prepared by completely soaking one strip in water, and then contacting it with a dry one, allowing time for the solutions to spread equally between them. Note that the upper housing 108 of the FIG. 7 instrument is hingedly mounted, much like the hinged mounting of the backing plate 82 of FIG. 6, to facilitate access. However, the housing 108 preferably is constrained from closing onto the lower structure by a minimal gap, as FIG. 7 shows.

EXAMPLE If

Fresh whole blood is tested for its concentration of Galactose using previously prepared reagent sites on type 903-C paper treated with a 6 milligrams/milliliters solution of polyox as above.

The reaction used is the enzymatic conversion of galactose to galactonic acid by galactose dehydrogenase, with the simultaneous conversion of Nicotinamide-adenine dinucleotide (NAD) to its reduced from NADH.

The galactose dehydrogenase (GDH) is obtained from the Boehringer Manheim Corporation as a suspension of 5 milligrams/milliliters in ammonium sulfate solution. The enzyme must be separated from the ammonium sulfate, which is done in an ultrafiltration cone obtained from the Amicon Corporation (Minicon 25). One hundred twenty microliters of the GDH suspension is placed in the ultrafiltration cone, and saline is added up to the 750 microliter mark.

The solution is then concentrated five times to the 150 microliter mark. This wash process is repeated two more times to yield a final solution concentrated ten times to 75 microliters. This process leaves the GDH in the cone, with the ammonium sulfate having passed through to waste.

The GDH in the cone is removed by adding Tris Buffer pH 6.2, 0.10M up to the 750 microliter mark, and pouring the solution from the cone into a container. The GDH concentration in the solution is approximately 5 I.U./ml. The reagent is completed by the addition of 6 mg of NAD.

The reagent strips are prepared by adding 15 microliters of this solution to preformed wells in the polyox treated paper as in Example Id, followed by vacuum drying.

It should be noted that a weal pH 6.2 buffer is used to displace the reaction off its maximum rate which occurs at pH 8. This is done to minimize the amount of the reaction which occurs during or after the ultrafiltration in the press, and before the reaction is restarted on the fluorometer.

To perform the galactose assay, the pre-treated wells are centered under the press, and covered with the ultra-filtration membrane and a sheet of untreated 903-C paper. A 20 microliter whole blood specimen is deposited on this top sheet, and the press closed for 75 to 100 seconds in order to achieve as high a transfer of galactose as possible. Saran wrap is also used in the press operation to eliminate sample contact with the press itself and its platen.

When the press is opened, the upper layers are stripped off and the reaction zone placed over the window of the fluorometer of FIG. 6. The reactants are reconstituted by the deposition of 11 microliters of a 0.2M pH 8.6 Tris Buffer, and the reaction monitored for several minutes.

The assay is calibrated by repeating the process with 20 microliters of various standard solutions substituted for the whole blood. The assay may also be run directly using centrifuged and separated serum, by depositing 10 microliters of diluted serum and 5 microliters of the pH 8.6 buffer on an unused reagent well.

A calibration curve was obtained by assaying different galactose standard solutions in place of whole blood. Eleven assays were performed on nine different solutions ranging in concentration from 0.0 to 90 Mg/Dl. Linear regression analysis yielded in correlation coefficient of 0.999, and showed that the chemistry in linear up to 90 Mg/Dl. The precision of the assay may be estimated from the difference of each of the measured points from the fitted line. The standard deviation of this difference is 1.48 Mg/Dl.

A standard recovery experiment was performed by adding galactose to four patient sera at several incremental values. The average recovery of 10 such additions to the four sera was 96 percent, with a standard deviation of 8 percent.

The foregoing glucose analysis has been performed successfully with a variety of fibrous sheets, including S&S 404, 595 and 25 papers, and the Whatman GF/A, GF/B and GF/C papers.

EXAMPLE II

Blood serum is tested for lactate concentration with a pre-prepared fibrous sheet, as of S&S 903-C paper with a wax ring about the test site. The sheet is prepared by first depositing, at the center of the test site, LDH in an ammonia suspension, such as Sigma Type III-Beef Heart. This is followed, without drying, by deposition at the same point of ten lambda of a water solution of fifteen milligrams of pyridine nucleotide (NAD) per milliliter with a trace of surfactant such as Brij. The sheet is then dried in a vacuum desiccator.

Where fresh serum is to be tested, the pre-prepared, but dried fibrous sheet is first treated by depositing ten lambda of glycine-hydrazine buffer at a pH of 9. This is followed, without drying, by the deposition of ten lambda of a ten-to-one dilution of the serum sample. The rate of NADH production as measured with a fluorometer in the manner of Example I identifies the lactate concentration within 5 percent of the amount determined by a reference procedure.

It has been found to be important in the preparation of the fibrous sheet that the LDH solution be added prior to the NAD solution, otherwise the lactate analysis occurs with significantly lesser sensitivity. It is believed that this is because the relatively heavy LDH molecules establish a bond with the fibers or otherwise resist spreading upon the subsequent addition of the lighter NAD molecules so that the two reagents largely occupy the same portion of the fibrous sheet. When the reagents are deposited in reverse order, it is believed that the lighter NAD molecules are moved laterally outward from the point of deposition by the heavier LDH molecules with the result that the spot on the sheet has a concentration of LDH molecules within a predominantly annular concentration of NAD molecules. The sensitivity is also observed to be diminished when the sequence of adding buffer and serum is reversed, i.e. when the sample serum is added before the buffer. (Note that the addition last of sample serum for the lactate analysis of this example is opposite to the preferred sequence for the glucose analysis of Example I.)

EXAMPLE III

As a third example, a fibrous sheet is again prepared in the manner of Example II, but the serum to be tested is available as a dried blot of whole blood carried on S&S 903-C test paper. The paper containing the whole blood sample is placed over the pre-prepared dry reagent sheet with an intervening untrafiltrate membrane, as described in the above-noted Ser. No. 243,028 application and illustrated herein in FIG. 4, and placed in the FIG. 4 press 32 also described in full in that application. Prior to closing the press, the blood stain is reconstituted. Where the stain is fresh, this is done by the addition of twenty lambda of Brij water or saline (0.9 percent normal NaCl solution). The press is then closed to transfer the serum ultrafiltrate through the intervening filter sheet to the reagent sheet. Alternatively, where the blood stain is not fresh, it is preferably reconstituted by the addition of twenty lambda of water with a trace of Brij or like surfactant, and then subjected to pressure to transfer it to the reagent sheet. Where the stain is old, it has been found desirable that an initial deposition of 25 to 30 lambda of diethyl ether to penetrate the clot immediately precede the Brij water.

In either case, the press is left closed for approximately one minute. The press transfers a known portion of the lactate in the sample to the reagent sheet, but typically insufficient liquid is transferred to provide sufficient molecular mobility for the reaction to proceed. Accordingly, the sheet that initially carried the blood sample and the intervening filter sheet are stripped from the reagent sheet, and twenty lambda of the glycine-hydrazine buffer (pH of 9) is applied to wet the lowermost reaction sheet. Again, the rate of NADH production is monitored with a fluorometer as set forth above.

For all of the foregoing tests, the fluorometer field of view is approximately a one square centimeter circular area centered on the point at which the reagents are deposited on the fibrous sheet.

The sample and reactant volumes set forth herein do not saturate a reaction site having this area.

EXAMPLE IV

As an illustration of the application of the invention to a more complex chemical reaction for blood analysis, a fibrous sheet of S&S 903-C paper is prepared as follows to test blood serum for the concentration of triglyceride. Again the basic chemical reactions for this analysis are known, as described for example in the above-noted brochure of Boehringer Mannheim Corporation under the heading "Neutral Fat (Triglycerides) and Glycerol." However, lipase is used to hydrolize the neutral fat to glycerol.

The first step in the preparation of the fibrous medium is to apply to the center of a reaction site on S&S 903-C paper 20 lambda of lipase (Schwartz-Mann No. 25) as a continuous stream or single droplet and allow it to dry. This is followed by the deposition at the same spot of twenty lambda of the enzyme solution glycerokinase-glycerophosphate dehydrogenose, and again the fibrous sheet is allowed to dry. Thereafter, ten lambda of a co-factor solution containing NAD and ATP, and the $Mg^{++}$ activator for glycerokinase and $Ca^{++}$ activator for lipase in Brij water solution of at least 3 milligrams per milliliter is deposited.

It should be noted that the three reagents so far added to the fibrous sheet have been added in the oder of decreasing molecular weight, i.e. the solution containing the lowest molecular-weight glycerophosphate dehydrogenase is added last. The remaining preparation of the fibrous sheet is to increase the concentration of the combined enzyme solution by successive depositions, so as not to unduly spread the material but rather to concentrate it over a limited area, e.g. one square centimeter, of the fibrous sheet. Accordingly, before the co-factor solution dries, another 10 lambda of the enzyme solution is deposited on the sheet and the sheet is then allowed to dry. Thereafter, 10 lambda of a glycine-hyrazine buffer of pH 9 is deposited on the sheet at the center of the reaction site followed by another 10 lambda of the enzyme solution and another drying step. The dry fibrous reaction sheet is now ready for use, and can be stored until needed.

To make a triglyceride analysis with the reagent sheet prepared in the foregoing manner, 10 lambda of the glycine-hydrazine buffer is first deposited on the sheet followed by 10 lambda of the blood serum being tested. The reaction site is then examined with a fluorometer for the rate of NADH production. A second test is performed with the same pre-prepared reaction sheet, but at a different spot or site, in the same manner except that ten lambda of saline are deposited in place of the sample serum, and the rate of NADH production measured in the same manner. The difference between the two rates of NADH production, each rate being relative to the background of the same site where that rate is measured, as measured one with the sample and the other with saline, is the desired measure of the triglyceride concentration. It is believed that such a differential measurement is needed to attain high accuracy due to impurities in the reagents and/or in the fibrous sheet forming the reaction and analysis vessel, and hence with pure materials the second, blank test can be eliminated.

The triglyceride concentration measured in the foregoing manner is within five percent of the concentration as determined with laboratory standard procedures.

Although the foregoing examples have involved analyses in which NADH is produced, the invention can equally be used in performing analyses in which a fluorophor is consumed, and the rate of consumption is monitored.

It will thus be seen that the objects set forth above, among those made apparent from the preceding description, are efficiently attained and, since certain changes may be made in carrying out the above method and in the constructions set forth without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described the invention, what is claimed as new and secured by Letters Patent is:

1. In the constituents analysis of sample material on a porous medium by reaction in a liquid state with reactants to produce a constituent-manifesting reaction product, the improvement comprising the steps of
   A. producing said reaction product at said analysis site with only an optically-thin concentration,
   B. illuminating said analysis site with incident electromagnetic radiation,
   C. sensing, from a field of view coincident with said analysis site, electromagnetic radiation that is resultant from said incident radiation and responsive to both the background response of said medium to said illumination and the concentration of said reaction product, and
   D. producing a sample-measuring signal in response to a differential function of said product-responsive sensed radiation and radiation resultant from incident radiation on said field of view and responsive to said background response of said medium at said analysis site and to said sample material and said reagents prior to said product-producing reaction.

2. In the constituent analysis of sample material on a porous medium by reaction with at least one reagent to produce a constituent-manifesting reaction product, the improvement comprising the steps of
   A. distributing said sample material and said reagent in liquid state over a selected analysis site of said medium,
   B. producing said reaction product at said analysis site with only an optically-thin concentration,
   C. illuminating said analysis site with incident electromagnetic radiation,
   D. sensing, from a field of view within said analysis site, electromagnetic radiation that is resultant from said incident radiation and responsive to the concentration of said reaction product, and
   E. measuring the rate of change of said radiation sensed during the production of said reaction product.

3. In a method as defined in claim 2, the further improvement in which said measuring step measures the rate of change of said radiation from a time after the cessation of spreading of liquids in said medium.

4. In a method as defined in claim 2, the further improvement in that said radiation is sensed substantially continuously during production of said reaction product, said distributing step includes balancing the amounts of said sample material and said reagents at said analysis site to produce a substantially uniform rate of reaction, and the further step of timing said measurement of rate of change to coincide with at least a portion of the duration of said uniform rate of reaction.

5. In the constituent analysis of sample material on a porous medium by reaction with at least one reagent to produce a constituent-manifesting reaction product, the improvement comprising the steps of
   A. distributing said sample material and said reagent in liquid state with substantially repeatable spatial distributions of concentration over a selected analysis site of said medium.
   B. producing said reaction product at said analysis site with only an optically-thin concentration,
   C. illuminating said analysis site with incident electromagnetic radiation,
   D. sensing, from a field of view within said analysis site, electromagnetic radiation that is resultant from said incident radiation and responsive to the concentration of said reaction product, and
   E. producing a measure of the constituent in response to radiation sensed from the same area within said site at at least two different times between which said reaction produces said reaction product.

6. In a method as defined in claim 5, the further improvement in that said step of producing said measure responds to a difference function of the radiation sensed at said different times.

7. In a method as defined in claim 5, the further improvement in which said sensing step comprises sensing fluorescence from said reaction product 8. In a method as defined in claim 5, the further improvement in which said medium has an unbounded test site.

9. In a method as defined in claim 5, the further improvement in that said distributing step distributes said sample material and said reagents in a concentration that does not saturate said medium at said analysis site.

10. In a method as defined in claim 5, the further step of maintaining the wetness of said reactants substantially the same at the times radiation is sensed for measurement.

11. In a method as defined in claim 5, the further step of maintaining a repeatable state of compression on said medium at said analysis site at the times radiation is sensed for measurement.

12. In a method as defined in claim 5, the further step of forming said porous medium with substantially non-wicking fibers at said analysis site.

13. In a method as defined in claim 5, the further steps of maintaining repeatable coupling of said incident radiation to said analysis site, and maintaining repeatable coupling of said resultant radiation from said site, at the times radiation is sensed for measurement.

14. In the constituent analysis of sample material on a porous medium by reaction with at least one reagent to produce a constituent-manifesting reaction product, the improvement comprising the steps of
   A. distributing said sample material and said reagent in liquid state with substantially repeatable spatial distributions of concentration over a selected analysis site of said medium, with at least one reactant selected from said sample material and one said reagent being provided at said site with a nonuniform spatial distribution of concentration,
   B. producing said reaction product at said analysis site with only an optically-thin concentration,
   C. illuminating said analysis site with incident electromagnetic radiation, and
   D. sensing, from a field of view within said analysis site, electromagnetic radiation that is resultant from said incident radiation and responsive to the concentration of said reaction product.

15. In a method as defined in claim 14, the further step of producing a measure of the concentration of a constituent in said sample in response to the integral of said sensed radiation over the area of at least a selected region of said test site.

16. A method of measuring the amount of a constituent of a soluble material sample comprising the steps of
   A. forming a repeatable concentration distribution over a test site of a porous support member of each chemical reactant that produces, upon chemical reaction with said sample, a reaction product identifying the concentration of said constituent, with at least one reagent distribution being nonuniform.
   B. forming a repeatable concentration distribution over said test site of said sample with a sufficiently low concentration to produce an optically-thin distribution of reaction product and allowing said sample to react, in liquid solution, with said reagents at said test site to produce said reaction product,
   C. sensing electromagnetic radiation emitted from said test site in response to incident energy and to the concentration of said reaction product thereat,
   D. integrating said sensed radiation emitted from at least a selected region of said test site, and
   E. producing an output measure in response to the change in said integral of sensed radiation resultant from said production of said reaction product.

17. A method as defined in claim 16 in which said distribution-forming step comprises applying at least some of said reagents to said test site in sequential order according to the molecular size of an active constituent of each reagent, starting with the reagent having the largest molecular constituent.

18. In chemical spot-test analysis employing a measured parameter responsive to concentration of a reaction-produced material at a test spot on a porous medium subsequent to deposition of liquid to the test spot, the improvement comprising the step of measuring the change in said parameter over a time interval during which said reaction produces said material in such small amount that the optical absorbance thereof at the wavelength of measurement changes by less than 0.2 throughout the monitored area of said test spot.

19. In chemical spot-test analysis as defined in claim 18, the further improvement comprising the step of maintaining the reaction-producing reactants at said monitored area of said test spot in a liquid condition of uniform wetness during said time interval.

20. In chemical spot-test analysis according to claim 19, the further improvement comprising the step of maintaining the state of compression of said medium, at least at said monitored area and contiguously therabout, uniform during said selected time interval.

21. In apparatus for measuring a selected product of reactants in liquid solution at test site on a porous medium and having means for subjecting said site to oscillating electromagnetic energy and for sensing energy which is responsive to said oscillating energy and to the presence of said selected reaction product, the improvement comprising
   A. measuring means for producing a measure of said sensed energy which is responsive to an optically-thin change in the concentration of said product at a single region of said site, and
   B. means for providing repeatable coupling of energy between said means for subjecting and said means for sensing, by way of said test site of said medium, at at least two times at which energy is sensed for measurement and between which said reactants produce said reaction product.

22. In apparatus as defined in claim 21, the further improvement in which said means for providing includes means for maintaining the wetness of said reactants at said test site substantially the same at said times of sensing energy for measurement.

23. In apparatus as defined in claim 21, the further improvement in which said means for maintaining includes means for sealing said test site of said medium to diminish evaporation of liquid therefrom.

24. In apparatus as defined in claim 21, the further improvement in which said means for providing includes means for maintaining said medium, at least at said test site, under a repeatable state of compression at said times of sensing energy for measurement.

25. In apparatus as defined in claim 21, the further improvement in which said measuring means includes
   A. A means for sensing said energy from said single region at two different times between which said reactants produce said selected product, and
   B. means for producing said measure in response to a difference function of the energy sensed at said different times.

26. In apparatus for measuring a selected reaction product of reactants at a test site on a sheet-like porous medium and having means for subjecting said site to oscillating electromagnetic energy and for sensing a selected parameter of energy which is responsive to said oscillating energy and to the presence of said selected reaction product, the improvement comprising
   A. support means for receiving said medium disposed with said test site within the field of view of said subjecting and sensing means, and for exposing said site for the receipt thereat of at least one reactant in liquid state for the production of said reaction product, and
   B. measuring means for producing a measure of said sensed energy responsive to a change, at a single monitored area of said site, in the concentration of said product which produces a change in the optical absorbance of said medium at the wavelength of measurement of less than 0.2 throughout the monitored area of said test spot.

27. In apparatus as defined in claim 26, the further improvement comprising means for maintaining the reactants at said test site in a liquid condition with uniform wetness during the production of said measured change in the concentration of said reaction product.

28. In apparatus as defined in claim 26, the further improvement comprising means for maintaining said test site of said medium at a repeatable location relative to said means for subjecting and said means for sensing, at least at times of sensing energy for said measurement.

29. In a photometric instrument for illuminating a reactant-bearing test site with incident electromagnetic energy and for measuring resultant electromagnetic energy emitted from said site in response to said incident energy with a parameter responsive to a selected reaction product of said reactants, when in liquid state, the improvement comprising
   A. first and second housing members
      1. arranged to receive between them a sheetlike carrier of said site with said first housing member facing a first side of said carrier and said second housing member facing a second opposite side of said carrier, and with said incident energy illuminating one side of said site and said resultant energy being sensed at at least one side of said site,
      2. one housing member being arranged for contiguous contact with both said carrier and said site,
      3. the other housing member being arranged for contact with the other side of said carrier and being normally spaced from the other side of said site,
      so that said contact of said housing members with said carrier sheet locates said carrier sheet relative to the path of said illuminated and resultant energy, and said contiguous abutment of one housing member with said site locates said site relative thereto, and
   B. means for sealing said test site at least during the sensing of resultant energy for measurement to diminish evaporation of liquid reactant therefrom.

30. In a photometric instrument according to claim 29, the further improvement comprising connection means joining said first and second housing means together for allowing said housing members to move apart to receive the sheet-like carrier of said site between them, and to move together into said contact with said carrier.

31. In chemical spot test analysis employing a measured parameter responsive to concentration of a reaction-produced material at a test spot on a fibrous medium, the improvement comprising the step of exposing at least said test spot of said fibrous medium, prior to the introduction of reaction-producing reagents to said test site, to an aqueous solution of a high molecular weight, crystalline, ethylene oxide polymer, said exposure being sufficient, after drying of said polymer solution, to diminish the absorption of liquid by the fibers of said medium.

32. In chemical spot test analysis as defined in claim 31, the further improvement comprising the step of drying said polymer solution on said fibrous medium subsequent to said exposing step and prior to introducing reaction-producing reactants to said test site.

33. In apparatus for measuring a selected product of chemical reactants at a test site on a fibrous medium and having means for subjecting said site to oscillating electromagnetic energy and for sensing a selected parameter of energy which is responsive to said oscillating energy and to the presence of said selected reaction product, the improvement comprising a substantially uniform fibrous structure in said fibrous medium within and contiguously beyond said reaction site, said structure consisting essentially of non-wicking fibrous material, and being characterized by the substantial termination of spreading therein of said reactants in liquid solution prior to the completion of said sensing of product-responsive energy.

34. In apparatus as defined in claim 33, the further improvement.
   A. comprising measuring means for sensing product-responsive energy for a selected interval during which said reactants produce said selected product at a substantially linear rate, and
   B. said uniform fibrous structure is further characterized by the substantial termination of spreading therein of said reactants in liquid solution significantly prior to the termination of said selected measuring interval.

35. In apparatus for measuring a selected product of chemical reactants at a test site on a fibrous medium and having means for subjecting said site to oscillating electromagnetic energy and for sensing a selected parameter of energy which is responsive to said oscillating energy and to the presence of said selected reaction product, the improvement wherein said fibrous medium consists essentially of paper-making fibers which are characterized by minimal absorption of liquid and are produced by treatment with a relatively high molecular weight polymer.

36. In apparatus for measuring a selected product of chemical reactants at a test site on a fibrous medium and having means for subjecting said site to oscillating electromagnetic energy and for sensing a selected parameter of energy which is responsive to said oscillating energy and to the presence of said selected reaction product, the improvement wherein said fibrous medium consists essentially of paper-making fibers which have been exposed to an aqueous solution of a high molecular weight, crystalline, ethylene oxide polymer and dried prior to the introduction thereto of said chemical reactants.

* * * * *

UNITED STATES PATENT AND TRADEMARK OFFICE
CERTIFICATE OF CORRECTION

PATENT NO. : 4,059,405
DATED : November 22, 1977
INVENTOR(S) : Lester A. Sodickson and Franklin Lim It is certified that error appears in the above-identified patent and that said Letters Patent are hereby corrected as shown below:

On the first page of the patent, under "References Cited", the applicant's name regarding Patent No. 3,526,480 should be spelled --Findl--.

Column 1, line 32, change "signficantly" to --significantly--.

Column 1, line 43, change "Pat." to --Pats.--.

Column 3, line 62, change "an" to --on--.

Column 5, lines 26 and 27, change "unqiue" to --unique--.

Column 9, line 67, change "dstributed" to --distributed--.

Column 11, lines 48 and 49, change "preferrd" to --preferred--.

Column 11, line 56, change "fluorescene" to --fluorescence--.

UNITED STATES PATENT AND TRADEMARK OFFICE
CERTIFICATE OF CORRECTION

PATENT NO. : 4,059,405

DATED : November 22, 1977

INVENTOR(S) : Lester A. Sodickson and Franklin Lim

It is certified that error appears in the above-identified patent and that said Letters Patent are hereby corrected as shown below:

Column 15, line 4, change "fo" to --for--.

Column 16, lines 64 and 65, change "fluoremeter" to --fluorometer--.

Column 17, line 11, change "radically" to --radially--.

Column 17, line 15, change "fluoroscent" to --fluorescent--.

Column 18, line 7, after "media" insert --which--.

Column 24, line 22, change "from" to --form--.

Column 24, line 50, change "weal" to --weak--.

Column 25, line 13, change "in" to --a--.

Column 26, line 10, change "untrafiltrate" to --ultrafiltrate--.

UNITED STATES PATENT AND TRADEMARK OFFICE
CERTIFICATE OF CORRECTION

PATENT NO. : 4,059,405             Page 3 of 3
DATED : November 22, 1977
INVENTOR(S) : Lester A. Sodickson and Franklin Lim It is certified that error appears in the above—identified patent and that said Letters Patent are hereby corrected as shown below:

Column 29, at the end of claim 7, add a period --.-- .

Column 30, line 37, before "test" insert --a--.

Column 31, line 3, before "means" delete "A".

Column 32, line 36, after "improvement" delete the period "." .

Signed and Sealed this

Twelfth Day of December 1978

[SEAL]

Attest:

RUTH C. MASON
Attesting Officer

DONALD W. BANNER
Commissioner of Patents and Trademarks

REEXAMINATION CERTIFICATE (161st)

United States Patent [19]
Sodickson et al.

[11] B1 4,059,405
[45] Certificate Issued Feb. 7, 1984

[54] METHOD AND APPARATUS FOR ANALYSIS OF CONSTITUENT CARRIED IN FIBROUS MEDIUM

[75] Inventors: Lester A. Sodickson, Newton, Mass.; Franklin Lim, Richmond, Va.

[73] Assignee: Damon Corporation, Needham Heights, Mass.

Reexamination Requests:
No. 90/000,171, Mar. 1, 1982
No. 90/000,312, Jan. 12, 1983

Reexamination Certificate for:
Patent No.: 4,059,405
Issued: Nov. 22, 1977
Appl. No.: 715,855
Filed: Aug. 19, 1976

Certificate of Correction issued Dec. 12, 1978.

Related U.S. Application Data

[63] Continuation-in-part of Ser. No. 243,068, Apr. 11, 1972, abandoned and a continuation-in-part of Ser. No. 498,646, Aug. 19, 1974, abandoned.

[51] Int. Cl.³ .................... G01N 21/24; G01N 33/16; G01N 21/64; G01N 35/00
[52] U.S. Cl. .................................. 436/44; 356/317; 422/56; 422/66; 422/67; 422/68; 436/34; 436/71; 436/95; 436/150; 436/169; 436/172
[58] Field of Search .......................... 422/52, 55–58, 422/66, 67, 69, 70, 34; 324/61 R; 356/317, 318, 434, 436; 428/539; 436/44, 34, 150, 169, 172

[56] References Cited

U.S. PATENT DOCUMENTS

| | | | |
|---|---|---|---|
| Re. 30627 | 5/1981 | Bagshawe et al. | 422/66 |
| 3,526,480 | 9/1970 | Findl et al. | 422/66 |
| 3,741,876 | 6/1973 | Guilbault et al. | 435/26 |

OTHER PUBLICATIONS

Demas, J. N. & Crosby, G. A., *The Journal of Physical Chemistry* (1971) vol. 75 (8), 991–1024.
Guilbault, G. G. *Fluorescence-Theory, Instrumentation & Practice* (1967) Marcel Dekker, Inc., New York.
Hezel, U. *Angew, Chem. Internat. Edit.* vol. 12 (1973) (4) pp. 298–306.
Hirs, C. H. W. (Editor) *Methods in Enzymology* (1967) Academic Press, New York, pp. 809, 810–812.
Klaus, R. *Journal of Chromatography,* vol. 16 (1964) pp. 322–326.
Parker, C. A. *Photoluminescence of Solutions* (1968) Elsevier Publishing Company, New York.
Pesce, A. J., Rosen, C. G. & Pasby, T. L. *Fluorescence Spectroscopy-An Introduction for Biology & Medicine* (1971) Marcel Dekker, Inc., New York.
Undenfriend, S. *Fluorescence Assay in Biology & Medicine,* vol. I (1962), vol. II (1969) Academic Press, New York.
Wang, C. H. & Willis, D. L., *Radiotracer Methodology in Biological Science* (1965) Prentice-Hall, Inc. New Jersey.
Wick, A. N., Barnet, H. N. & Ackerman, N., *Analytical Chemistry* (1949) vol. 21 (12), 1511–1513.
Yankwich, P. E., Norris, T. H. & Huston, J. *Analytical Chemistry* (1949) vol. 19 (7), 439–441.

*Primary Examiner*—Michael S. Marcus
*Attorney, Agent, or Firm*—John A. Lahive, Jr.; W. Hugo Liepmann

[57] ABSTRACT

An optically-thin preparation of a sample solution and chemical reagents produces a constituent-manifesting reaction product that can be measured in linear relation to the concentration of the constituent of interest. A fibrous sheet contains the sample and the reagents for both the reaction and the measurement. The same site on the fibrous sheet which bears the reacting materials serves as a blank to produce a reference signal for the measurement.

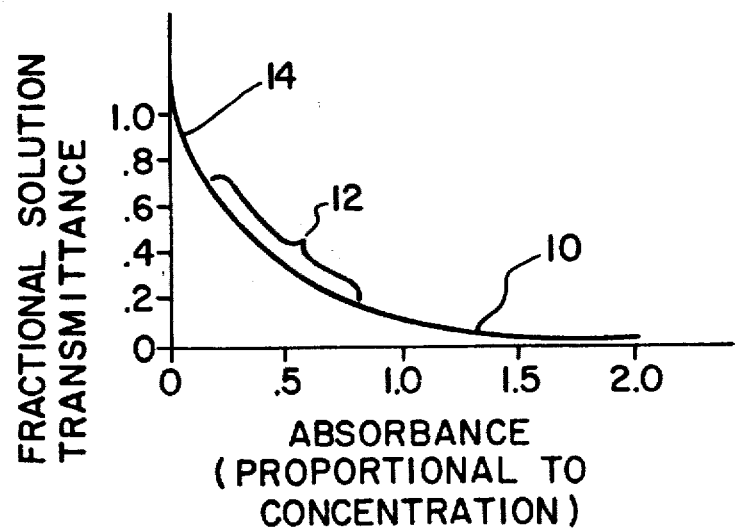

REEXAMINATION CERTIFICATE ISSUED UNDER 35 U.S.C. 307.

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 31, 32 and 36 is confirmed.

Claim 25 having been finally determined to be unpatentable, is cancelled.

Claims 1, 2, 5, 13, 14, 16, 18, 21–23, 26–29 and 33–35 are determined to be patentable as amended:

Claims 3–4, 6–12, 15, 17, 19, 20, 24 and 30, dependent on an amended claim, are determined to be patentable.

New claims 37–39 are added and determined to be patentable.

1. In the constituents analysis of sample material on a porous medium, by reaction in a liquid state with reactants to produce a constituent-manifesting reaction product *and wherein the medium is absorbent to the sample in liquid state*, the improvement comprising the steps of
   A. producing said reaction product *within said porous medium* at said analysis site with only an optically-thin concentration,
   B. illuminating said analysis site with incident electromagnetic radiation,
   C. sensing, from a field of view coincident with said analysis site, electromagnetic radiation that is resultant from said incident radiation and responsive to both the background response of said medium to said illumination and the concentration of said reaction product, and
   D. producing a sample-measuring signal in response to a differential function of said product-responsive sensed radiation and radiation resultant from incident radiation on said field of view and responsive to said background response of said medium at said analysis site and to said sample material and said reagents prior to said product-producing reaction.

2. In the constituent analysis of sample material on a porous medium by reaction with at least one reagent to produce a constituent-manifesting reaction product, the improvement comprising the steps of
   A. distributing said sample material and said reagent in liquid state over a selected analysis site of said medium, *with said medium being absorbent to the sample in liquid state*,
   B. producing said reaction product, *by reaction in liquid state, within said porous medium* at said analysis site with only an optically-thin concentration,
   C. illuminating said analysis site with incident electromagnetic radiation,
   D. sensing, from a field of view within said analysis site, electromagnetic radiation that is resultant from said incident radiation and responsive to the concentration of said reaction product, and
   E. measuring the rate of change of said radiation sensed during the production of said reaction product.

5. In the constituent analysis of sample material on a porous medium by reaction with at least one reagent to produce a constituent-manifesting reaction product, the improvement comprising the steps of
   A. distributing said sample material and said reagent in liquid state with substantially repeatable spatial distributions of concentration over a selected analysis site of said medium, *with said medium being absorbent to the sample material in liquid state*,
   B. producing said reaction product, *by reaction in liquid state, within said porous medium* at said analysis site with only an optically-thin concentration,
   C. illuminating said analysis site with incident electromagnetic radiation,
   D. sensing, from a field of view within said analysis site, electromagnetic radiation that is resultant from said incident radiation and responsive to the concentration of said reaction product, and
   E. producing a measure of the constituent in response to radiation sensed from the same area within said site at at least two different times between which said reaction produces said reaction product.

13. In a method as defined in claim 5, the further steps of maintaining repeatable *and time-wise uniform* coupling of said incident radiation to said analysis site, and maintaining repeatable *and time-wise uniform* coupling of said resultant radiation from said site, at the times radiation is sensed for measurement.

14. In the constituent analysis of sample material on a porous medium by reaction with at least one reagent to produce a constituent-manifesting reaction product, the improvement comprising the steps of
   A. distributing said sample material and said reagent in liquid state with substantially repeatable spatial distributions of concentration over a selected analysis site of said medium, *with said medium being absorbent to said sample in liquid state and* with at least one reactant selected from said sample material and one said reagent being provided at said site with a nonuniform spatial distribution of concentration,
   B. producing said reaction product, *by reaction in liquid state, within said porous medium* at said analysis site with only an optically-thin concentration,
   C. illuminating said analysis site with incident electromagnetic radiation, and
   D. sensing, from a field of view within said analysis site, electromagnetic radiation that is resultant from said incident radiation and responsive to the concentration of said reaction product.

16. A method of measuring the amount of a constituent of a soluble material sample comprising the steps of
   A. forming a repeatable concentration distribution over a test site of a porous support member of each chemical reactant that produces, upon chemical reaction with said sample, a reaction product identifying the concentration of said constituent, with at least one reagent distribution being nonuniform,
   B. forming a repeatable concentration distribution over said test site of said sample with a sufficiently low concentration to produce an optically-thin distribution of reaction product and allowing said sample to react, in liquid solution, with said reagents at said test site to produce said reaction product *within said porous member, with said medium being absorbent to said sample in said liquid solution,*

C. sensing electromagnetic radiation emitted from said test site in response to incident energy and to the concentration of said reaction product thereat, D. integrating said sensed radiation emitted from at least a selected region of said test site, and E. producing an output measure in response to the change in said integral of sensed radiation resultant from said production of said reaction product.

18. In chemical spot-test analysis employing a measured parameter responsive to concentration of a reaction-produced material, *by reaction in liquid state,* at a test spot on a porous medium subsequent to deposition of liquid to the test spot, *with the medium being absorbent to said liquid at the test spot,* the improvement comprising the step of measuring the change in said parameter over a time interval during which said reaction produces said material *within said porous medium* in such small amount that the optical absorbance thereof at the wavelength of measurement changes by less than 0.2 throughout the monitored area of said test spot.

21. In apparatus for measuring a selected product of reactants in liquid solution at *a* test site on a porous medium and having means for subjecting said site to oscillating electromagnetic energy and for sensing energy which is responsive to said oscillating energy and to the presence of said selected reaction product, the improvement comprising A. measuring means for producing, *with a medium that is absorbent to the reactants in said liquid solution,* a measure of said sensed energy which is responsive to an optically-thin change in the concentration of said product *within said porous medium* at a single region of said site, and B. means for providing repeatable *and uniform* coupling of energy between said means for subjecting and said means for sensing, by way of said test site of said *porous* medium, at at least two times at which energy is sensed for measurement and between which said reactants produce said reaction product, *said providing means including means for retarding evaporation of said liquid solution from said test site between said times of energy sensing.*

22. In apparatus as defined in claim 21, the further improvement in which said means for providing includes means for [maintaining the wetness of said reactants at said test site substantially the same at said times of sensing energy for measurement] *heating the apparatus for diminishing the condensation in the apparatus of vapors of said liquid solution.*

23. In apparatus as defined in claim 21, the further improvement in which said means for [maintaining] *providing* includes means for sealing said test site of said medium *within a substantially vapor-tight space* to diminish evaporation of liquid therefrom.

26. In apparatus for measuring a selected reaction product of reactants at a test site on a sheet-like porous medium and having means for subjecting said site to oscillating electromagnetic energy and for sensing a selected parameter of energy which is responsive to said oscillating energy and to the presence of said selected reaction product, the improvement comprising A. support means for receiving said medium disposed with said test site within the field of view of said subjecting and sensing means, and for exposing said site for the receipt thereat of at least one reactant in liquid state for the production of said reaction product *within said porous medium by reaction in liquid state, with said medium being absorbent to said reactant in liquid state,* [and]

B. *means for retarding the loss of liquid from said test site of said medium for maintaining reactants at said test site in a liquid condition with uniform wetness during the production of said measured change in the concentration of said reaction product, and*

[B.] C. measuring means for producing a measure of said sensed energy responsive to a change, at a single monitored area of said site, in the concentration of said product *within said porous medium* which produces a change in the optical absorbance of said medium at the wavelength of measurement of less than 0.2 throughout the monitored area of said test spot.

27. In apparatus as defined in claim 26, the further improvement [comprising means for maintaining the reactants at said test site in a liquid condition with uniform wetness during the production of said measured change in the concentration of said reaction product] *wherein said means for retarding includes means for sealing said medium at said test site within a substantially vapor-tight space.*

28. In apparatus as defined in claim 26, the further improvement [comprising means for maintaining said test site of said medium at a repeatable location relative to said means for subjecting and said means for sensing, at least at times of sensing energy for said measurement] *comprising heating means for diminishing the condensation in the apparatus of vapors of said reactants in liquid state.*

29. In a photometric instrument for illuminating a reactant-bearing test site with incident electromagnetic energy and for measuring resulting electromagnetic energy emitted from said site in response to said incident energy with a parameter responsive to a selected reaction product of said reactants, when in liquid state, the improvement comprising A. first and second housing members
  1. arranged to receive between them a sheetlike carrier of said site with said first housing member facing a first side of said carrier and said second housing member facing a second opposite side of said carrier, and with said incident energy illuminating one side of said site and said resultant energy being sensed at at least one side of said site,
  2. one housing member being arranged for contiguous contact with both said carrier and said site,
  3. the other housing member being arranged for contact with the other side of said carrier and being normally spaced from the other side of said site, so that said contact of said housing members with said carrier sheet locates said carrier sheet relative to the path of said illuminated and resultant energy, and [said contiguous abutment of one housing member with said site] locates said site relative thereto, and B. [means for sealing said test site] *sealing means arranged together with said housing members for enclosing said medium at said test site within a substantially vapor-tight space to diminish evaporation of said liquid reactants,* at least during the sensing of resultant energy for measurement [to diminish evaporation of liquid reactant therefrom].

33. In [apparatus for measuring] *the measurement of a selected product of chemical reactants in liquid state* at a test site on [a] *a* fibrous medium [and having means for] *with the steps of* subjecting said site to oscillating electromagnetic energy and [for] sensing a selected parameter of energy which is responsive to said oscillating energy and to the presence of said selected reaction product, the improvement comprising *the steps of*
  A. *providing* a substantially uniform fibrous structure in said fibrous medium within and contiguously beyond said reaction site, *and further providing* said structure *to be absorbent to the reactants in such liquid state and to consist* [consisting] essentially of non-wicking fibrous material, and [being characterized by the substantial termination of]
  B. *terminating substantially the* spreading [therein] *in said fibruous medium* of said reactants in liquid solution prior to the completion of said sensing of product-responsive energy for *effecting such measurement with an optically thin concentration of said reaction product held in interstices of said medium with substantially constant wetness.*

34. In [apparatus] *measurement* as defined in claim 33, the further improvement
  A. comprising [measuring means for] sensing product-responsive energy for a selected interval during which said reactants produce said selected product *within said fibrous medium* at a substantially linear rate, and
  B. [said uniform fibrous structure is further characterized by the] *wherein said* substantial termination of spreading [therein of said reactants in liquid solution] *occurs* significantly prior to the termination of said selected measuring interval.

35. In [apparatus for measuring a selected product of chemical reactants at a test site on a fibrous medium and having means for subjecting said site to oscillating electromagnetic energy and for sensing a selected parameter of energy which is responsive to said oscillating energy and to the presence of said selected reaction product, the improvement wherein] *measurement according to claim 33, the further step of providing* said fibrous medium [consists] essentially of paper-making fibers which are characterized by minimal absorption of liquid and are produced by treatment with a relatively high molecular weight polymer.

37. *In constituent analysis according to claim 1, the further improvement comprising the step of providing the wetness of said medium at said analysis site at a level which ceases spreading within said medium substantially prior to said sensing of radiation for the production of said measuring signal.*

38. *In constituent analysis according to claim 1, the further improvement comprising the step of controlling said product-producing reaction for producing said product at a known rate substantially after the cessation of spreading of liquid in said medium at said analysis site.*

39. *In chemical spot test analysis according to claim 18 by measuring said change by illuminating said test spot with incident electromagnetic radiation and by sensing electromagnetic radiation that is resultant from said incident radiation and responsive to the concentration of said reaction product, the further improvement comprising the steps of maintaining the coupling of said incident radiation to said test spot, and the coupling of said resultant radiation from said test spot, uniform over said time interval and repeatable.*

* * * * *